(12) United States Patent
Moats et al.

(10) Patent No.: US 9,173,590 B2
(45) Date of Patent: Nov. 3, 2015

(54) METHOD AND SYSTEM FOR QUANTITATIVE RENAL ASSESSMENT

(75) Inventors: Rex Moats, Pasadena, CA (US); Yang Tang, Los Angeles, CA (US); Priyank Sharma, Philadelphia, PA (US); Hollie Jackson, Yorba Linda, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 193 days.

(21) Appl. No.: 13/697,757

(22) PCT Filed: May 17, 2011

(86) PCT No.: PCT/US2011/036797
§ 371 (c)(1),
(2), (4) Date: Dec. 17, 2012

(87) PCT Pub. No.: WO2011/146475
PCT Pub. Date: Nov. 24, 2011

(65) Prior Publication Data
US 2013/0084246 A1    Apr. 4, 2013

Related U.S. Application Data

(60) Provisional application No. 61/345,558, filed on May 17, 2010.

(51) Int. Cl.
*A61B 5/05* (2006.01)
*A61B 5/055* (2006.01)
(Continued)

(52) U.S. Cl.
CPC ............... *A61B 5/055* (2013.01); *A61K 49/06* (2013.01); *A61M 5/007* (2013.01); *G06T 7/0012* (2013.01); *G06T 2207/10088* (2013.01); *G06T 2207/30084* (2013.01)

(58) Field of Classification Search
CPC ....... A61B 5/055; A61K 49/06; A61M 5/007; A61T 7/0012; G06T 2207/30084; G06T 2207/10088
USPC ........................................................ 600/410
See application file for complete search history.

(56) References Cited

U.S. PATENT DOCUMENTS 4,945,478 A    7/1990  Merickel et al.
6,671,540 B1   12/2003 Hochman
(Continued)

FOREIGN PATENT DOCUMENTS

WO      2009058915 A1    5/2009
WO      WO2011146475     11/2011

OTHER PUBLICATIONS

Zollner (Zoellner) et la., Assessment of 3D DCE-MRI of the kidneys using non-rigid image registration and segmentation of voxel time courses, Computerized Medical Imaging and Graphics, 33, Apr. 2009, 171-181.*

(Continued)

*Primary Examiner* — Bo J Peng
(74) *Attorney, Agent, or Firm* — Hema Vakharia-Rao; Nixon Peabody LLP

(57) ABSTRACT

Method and system embodiments of the present invention employ computational analysis tools running on one or more computer systems to quantitatively analyze MRI data from patients in order to both assess various functional parameters and characteristics of a patient's kidney, as well as to provide an electronic display device interconnected with the one or more computer systems, and accessible visualization of the quantitative assessment to facilitate diagnosis of various types of kidney abnormalities and pathologies.

11 Claims, 27 Drawing Sheets

(51) Int. Cl.
  *G06T 7/00* (2006.01)
  *A61K 49/06* (2006.01)
  *A61M 5/00* (2006.01)

(56) References Cited

U.S. PATENT DOCUMENTS

| | | | |
|---|---|---|---|
| 7,668,359 | B2 | 2/2010 | Battle |
| 2004/0064037 | A1 | 4/2004 | Smith |
| 2005/0201601 | A1 | 9/2005 | Sun et al. |
| 2007/0165921 | A1 | 7/2007 | Agam et al. |
| 2009/0143669 | A1 | 6/2009 | Harms et al. |

OTHER PUBLICATIONS

Ding et al., K-means Clustering via Principal Component Analysis, Proceedings of the 21st International Conference on Machine Learning, Banff, Canada, 2004.*

Su et al., In Search of Deterministic Methods for Initializing K-Means and Gaussian Mixture Clustering, Department of Electrical and Computer Engineering Northeastern University, Boston, Sep. 24, 2006.*

IPRP for PCT/US2011/036797.

ISR for PCT/US2011/036797.

Written Opinion for PCT/US2011/036797.

Abdelmunim et al. A Kidney Segmentation Approach from DCE-MRI Using Level Sets. IEEE (2008); 6 pages.

Anderlik et al. Quantitative assessment of kidney function using dynamic contrast enhanced MRI—Steps towards an integrated software prototype. Proceedings of the 6th International Symposium on Image and Signal Processing and Analysis (2009). 575-581.

Erdt et al. Smart manual landmarking of organs. Proc of SPIE (2010). 7623: 9 pages.

Hennemuth et al. A comprehensive approach to the analysis of contrast enhanced cardiac MR Images. IEEE Transactions on Medical Imaging (2008). 27(11): 1592-1610.

Li et al. A new 3D model-based minimal path segmentation method for kidney MR Images. IEEE (2008); 2342-.

Song et al. Four dimensional MR Image analysis of dynamic renography. Proceedings of the 28th IEEE, EMBS Annual International Conference (2006). 3134-3137.

Yuksel et al. A Kidney Segmentation Framework for Dynamic Contrast Enhanced Magnetic Resonance Imaging. 10 pages.

Zollner et al. Assessment of 3D DCE-MRI of the kidneys using non-rigid image registration and segmentation of voxel time courses. Computerized Medical Imaging and Graphics (2009. 33:171-181.

* cited by examiner

Figure 1
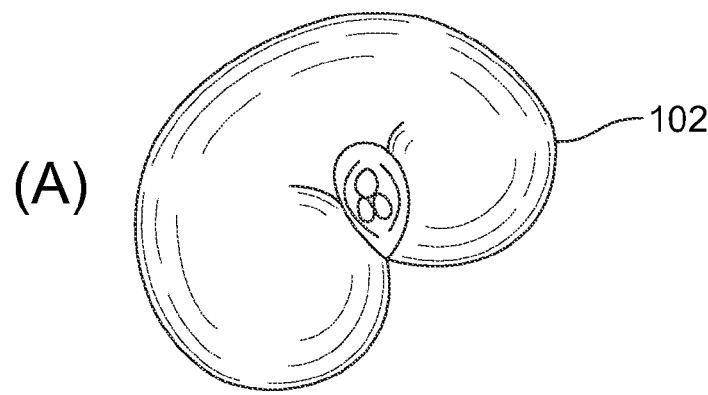
(A)
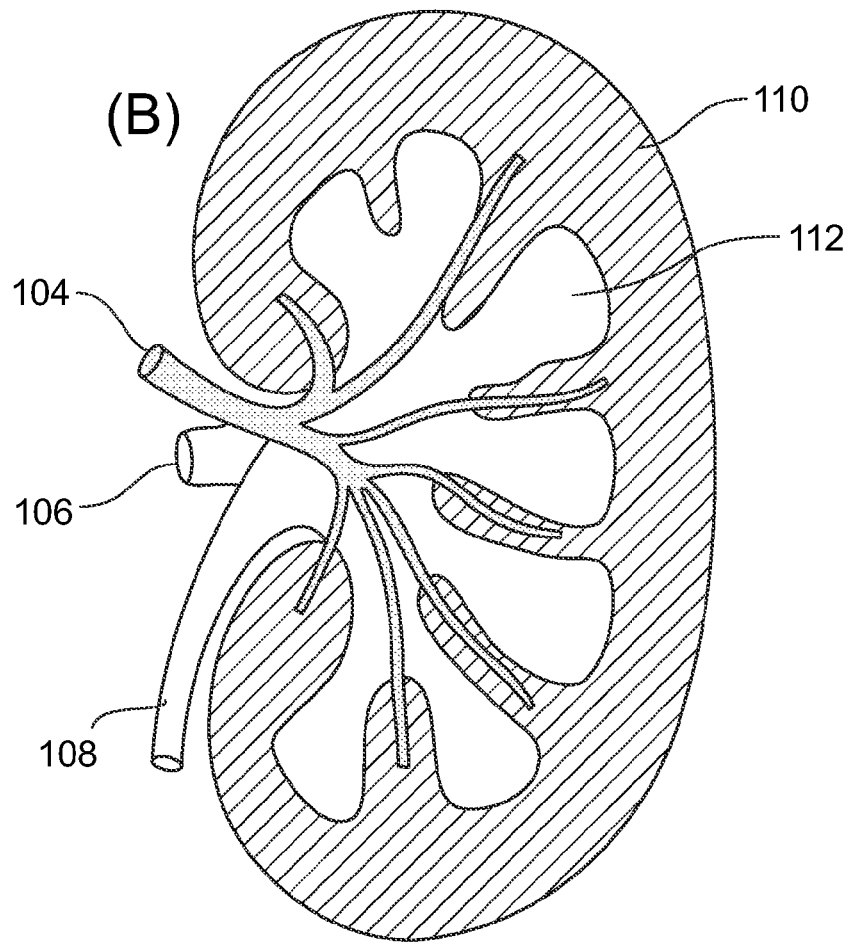
(B)

(A)  Main steps in workflow

METHOD AND SYSTEM FOR QUANTITATIVE RENAL ASSESSMENT

CROSS-REFERENCE TO RELATED APPLICATIONS

This application is the National Phase of International Application PCT/US2011/36797, filed May 17, 2011, which designated the U.S. and that International Application was published under PCT Article 21(2) in English. The present application also claims the benefit of the filing date of U.S. Provisional Application No. 61/345,558, filed May 17, 2010, the disclosures of each of which are incorporated herein by reference in their entirety.

FIELD OF INVENTION

The present invention is related to medical-imaging analysis and, in particular, to an automated and/or semi-automated method for quantitative assessment of renal function and morphology from a time series of magnetic-resonance images ("MRIs") of a kidney. The invention furthers the practice of evidence based medicine by providing objective analysis of the normal abnormal and irrelevant.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Over the years, many different techniques have been developed and applied for imaging kidneys. Early techniques involved radiation-opaque dyes injected into a patient followed by a time series of X-rays that allowed a diagnostician to observe the passage of the radiation-opaque dyes through the kidney. These techniques were entirely manual, requiring physical display of the images and laborious interpretation by the diagnostician. More recently, automated imaging techniques have been developed to provide high-resolution, three-dimensional images of various organs.

Dynamic contrast enhanced magnetic resonance imaging (DCE-MRI) is a noninvasive way to gain insight into both the anatomic and functional conditions of the kidney. Because previous studies have revealed a good correlation between MRI and radionuclear scintigraphy results, DCE-MRI has the potential to be the predominant method in kidney diagnosis. Moreover, this technique is especially beneficial for children because it does not use radioactivity and provides higher resolutions than nuclear scans. The quantitative assessment based on the renal DCE-MRI is foreshadowed in pediatric diagnosis.

Both morphological and functional parameters are important for clinical decisions in pediatric kidney diseases. For morphological features, kidney volume is important and computationally accessible, which is effective in disease decision trees. Nearly all patients diagnosed will undergo a renal size measurement (3). As well, the shape and position of the cortex, medulla and other tissues provide useful information for diagnosis.

To acquire functional parameters, kinetic models are used and studied. Based on first order kinetics, two compartment models, which include a vascular and a tubular compartment, are usually used to simulate the renal physical mechanisms of the kidney. The flux is considered to be unidirectional in the two compartment model through glomerular filtration, which can be measured by the Patlak-Ruland plot technique. In later research, the outflow from the tubules is taken into account, which has an improved correlation with clearance results. Recently, the multiple compartment model is also proposed and the preliminary results are reported, which concern a more detailed description of the nephron system.

However, the complexity of renal physiology and variance in imaging techniques sometimes complicates the implementation of a sophisticated model approaching a realistic kidney, which limits the application of those models. The addition of compartments does not necessarily result in an increase of performance. Therefore, model free methods are adopted as well.

The model free methods mainly focus on the individual time intensity curves (TICs). Many parameters such as mean transit time and maximum upslope can be directly calculated from TICs. According to the curve shape, model free methods try to distinguish normal tissue from abnormal tissue, which in turn is related to pathological findings. Compared to physiological models, model free methods are less sensitive to the protocol and supply a more detailed pixel by pixel (or voxel) analysis.

To create a flexible and comprehensive assessment tool for pediatric renal disease studies, the inventors employed a cluster based method and presented the post processing procedures. The major 4 stages of the post processing are displayed in FIG. 1. After preprocessing, the dynamical data are grouped into three dimensional (3D) clusters according to their activity similarities as judged by time intensity curves. When applying the anatomical and functional knowledge, the clusters are automatically recognized to be either part of the kidney or not, and then the kidney is segmented into different inner compartments. In the third stage, both global and local parameters are calculated with optional definitions. Finally, both anatomical and functional features are displayed in an intuitive form for visualization by clinicians.

Compared to the traditional two dimensional (2D) regions of interest (ROI), the 3D clusters have a more precise description of similar tissues while reducing the number of areas of interests. The automatic segmentation based on clusters has a greater capacity to deal with misshapen tissues due to the disorders, which alleviates clinicians from tedious manual delineations. The cluster number can be adjusted and parameters can be selected for different research purposes and clinical protocols.

SUMMARY OF THE INVENTION

The invention furthers the practice of evidence based medicine by providing objective analysis of the normal abnormal and irrelevant. Method and system embodiments of the present invention employ computational-analysis components running on one or more computer systems to quantitatively analyze MRI data from a patient in order to both assess various functional parameters and characteristics of the patient's kidney, as well as to provide, on an electronic display device interconnected with the one or more computer systems, an accessible visualization of the quantitative assessment to facilitate diagnosis of various types of kidney abnormalities and pathologies.

The invention provides a quantitative renal assessment system comprising (a) a computer system, (b) a time series of MRI images obtained in the absence and presence of an MRI contrast-enhancing substance, stored as a dataset within the computer system, wherein the dataset comprises intensities associated with voxels at each time point in the time series of MRI images and (c) a quantitative renal assessment component, executing on one or more processors of the computer system, which generates an assessment of a kidney imaged in the time series of MRI images. The quantitative organ assessment component generates an assessment of the organ imaged in the time series of MRI images by (i) compressing the dataset to fewer dimensions, (ii) partitioning voxels within the dataset into clusters, each cluster containing voxels with similar time-intensity curves, and (iii) computing functional characteristics and parameters of the organ from aggregate intensity-versus-time characteristics of the voxels within the clusters. In an embodiment, the quantitative organ assessment may be visually displayed.

The invention further provides a method for assessing kidney function in a subject comprising (a) acquiring a pre-contrast $T_0$ MRI image, (b) injecting an MRI contrast-enhancing substance into the kidney of the subject, (c) obtaining a quantitative-renal-assessment of the subject using the quantitative-renal-assessment system described above, (d) visually displaying the quantitative-renal-assessment, (e) comparing at least one morphological and/or functional parameter from the quantitative-renal-assessment to that of a control subject, and (f) diagnosing a presence or absence of abnormal kidney function in the subject wherein a difference in at least one morphological and/or functional parameter between the subject and the control subject is indicative of abnormal kidney function in the subject. In an embodiment, the quantitative organ assessment may be visually displayed.

BRIEF DESCRIPTION OF THE DRAWINGS

FIGS. 1A-B depict a human kidney.

FIGS. 6A-7B depict the principal-component-analysis technique that allows for a high-dimension dataset to be compressed into a dataset with lower dimensionality.

DETAILED DESCRIPTION OF THE INVENTION

Figure 2:
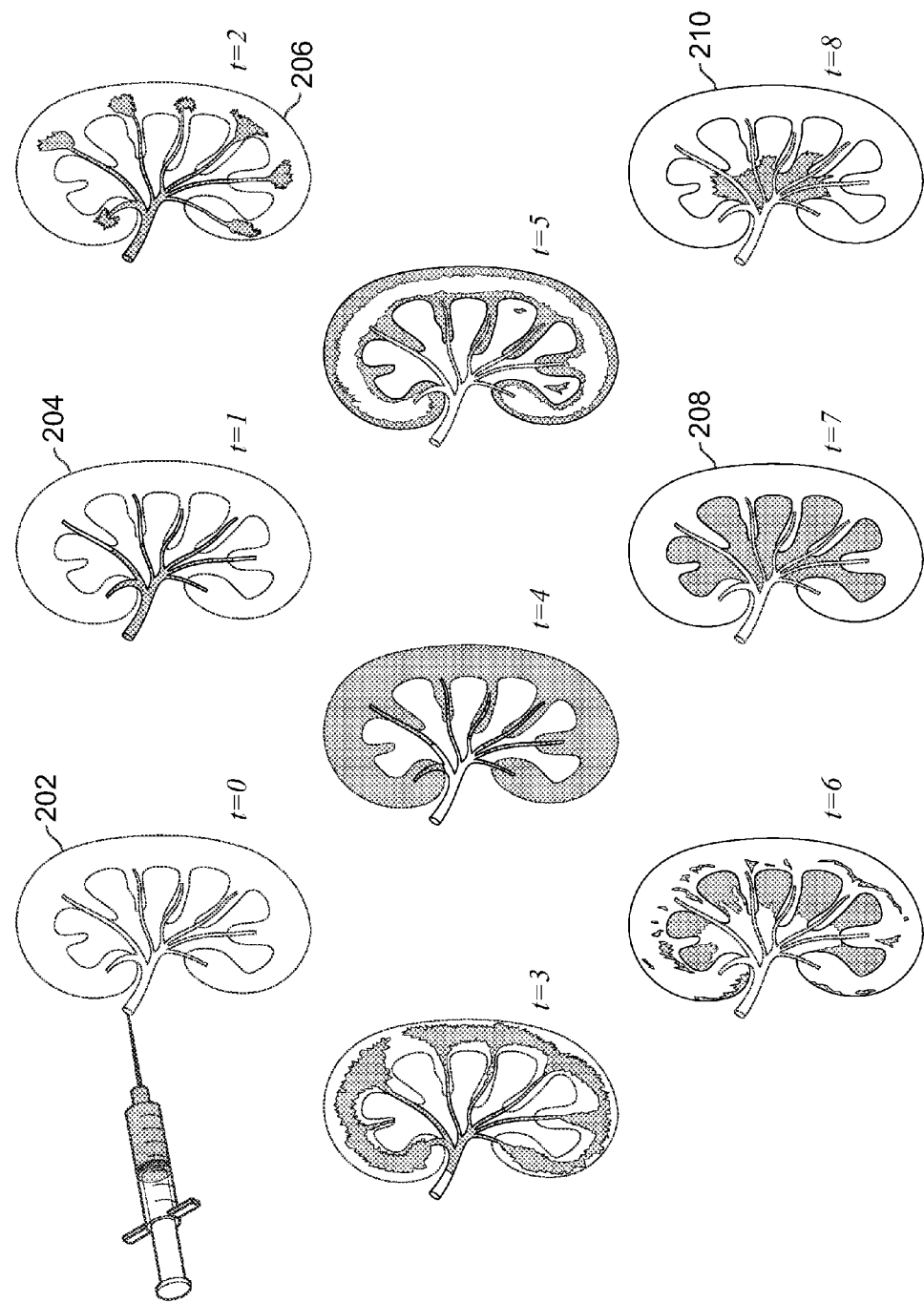
FIG. 2 depicts the process by which a time series of MRIs are acquired from a patient.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

The invention furthers the practice of evidence based medicine by providing objective analysis of the normal abnormal and irrelevant. As discussed above, DCE-MRI is a particularly attractive imaging method that employs MRI imaging technology, in combination with injection of an MRI-contrast-enhancing substance, to produce a time series of three-dimensional MRI images of an organ in which entry of the contrast-enhancing substance into the kidney and elimination of the contrast-enhancing substance from the kidney can be followed over a period of time. The contrast-enhancing substance generates the bulk of the MRI signal, reflected in voxel intensities. Time-intensity curves (TICs") for different parts of the kidney reflect the change in concentration of the contrast-enhancing substance in the different parts of the kidney over time, and are related to the flow of fluids through the different parts of the kidney. The TICs can, in turn, be used to compute a variety of different functional parameters and characteristics for a kidney, which can reveal various abnormal conditions and pathologies. The amount of data collected in a typical MRI time series is enormous. Moreover, visualizing three-dimensional images over time is a challenging undertaking, even with the help of sophisticated computational visualization tools. Automated and/or semi-automated methods for processing raw MRI time-series data in order to extract functional parameters and characteristics of an imaged kidney, as well as to provide intuitively annotated visualization of a kidney that is quickly and straightforwardly accessible to a diagnosticians, are sought by designers and manufacturers of imaging technology, diagnosticians, hospitals and laboratories, research organizations, and, ultimately, patients needing assessment of the function of their kidneys. In addition to the kidney, the DCE-MRI imaging technique may also be used for other organs such as abdomen, brain, breast, heart, liver, lung, neck, pelvis, the musculoskeletal system, ovaries, spine and/or prostate.

The invention provides a quantitative organ assessment system comprising (a) a computer system, (b) a time series of MRI images obtained in the absence and presence of an MRI contrast-enhancing substance, stored as a dataset within the computer system, wherein the dataset comprises intensities associated with voxels at each time point in the time series of MRI images and (c) a quantitative organ assessment component, executing on one or more processors of the computer system, which generates an assessment of the organ imaged in the time series of MRI images. The quantitative organ assessment component generates an assessment of the organ imaged in the time series of MRI images by (i) compressing the dataset to fewer dimensions, (ii) partitioning voxels within the dataset into clusters, each cluster containing voxels with similar time-intensity curves, and (iii) computing functional characteristics and parameters of the organ from aggregate intensity-versus-time characteristics of the voxels within the clusters. In an embodiment, the quantitative organ assessment may be visually displayed. In another embodiment, the organ is any one or more of abdomen, brain, breast, heart, liver, lung, neck, pelvis, the musculoskeletal system, ovaries, spine and/or prostate.

The invention also provides a quantitative renal assessment system comprising (a) a computer system, (b) a time series of MRI images obtained in the absence and presence of an MRI contrast-enhancing substance, stored as a dataset within the computer system, wherein the dataset comprises intensities associated with voxels at each time point in the time series of MRI images and (c) a quantitative renal assessment component, executing on one or more processors of the computer system, which generates an assessment of a kidney imaged in the time series of MRI images. The quantitative organ assessment component generates an assessment of the organ imaged in the time series of MRI images by (i) compressing the dataset to fewer dimensions, (ii) partitioning voxels within the dataset into clusters, each cluster containing voxels with similar time-intensity curves, and (iii) computing functional characteristics and parameters of the organ from aggregate intensity-versus-time characteristics of the voxels within the clusters. In an embodiment, the quantitative organ assessment may be visually displayed.

In an embodiment of the invention, the quantitative organ assessment system further comprises an MRI contrast-enhancing substance, for example gadolinium-DTPA (Gd-DTPA), ProHance (gadoteridol), Gd-DOTA, Gd-EDTA, Gd-labeled antibodies, monoclonal antibodies (McAB) and/or TTPS4.

In addition to DCE-MRI, the methodology described and claimed herein may be used with other modalities such as computer tomography (CT) scanning, Ultrasound, Magnetic Resonance (MR), Radiotracing methods and/or with methods which use optical exogenous agents. The instant methodology may also be used with methods which produce inherent contrast if there is a variation through time, for example, during a disease process. The instant methodology may also be used with systems which permit perturbations (adding contrast agents) like shining light or us waves into the organ and with any cross-section imaging modalities that have a time-dependent contrast intensity.

The invention further provides a method for assessing kidney function in a subject comprising (a) acquiring a pre-contrast $T_0$ MRI image, (b) injecting an MRI contrast-enhancing substance into the kidney of the subject, (c) obtaining a quantitative-renal-assessment of the subject using the quantitative-renal-assessment system described above, (d) visually displaying the quantitative-renal-assessment, (e) comparing at least one morphological and/or functional parameter from the quantitative-renal-assessment to that of a control subject, and (f) diagnosing a presence or absence of abnormal kidney function in the subject wherein a difference in at least one morphological and/or functional parameter between the subject and the control subject is indicative of abnormal kidney function in the subject. In an embodiment, the quantitative organ assessment may be visually displayed.

The invention also provides a method for determining the prognosis of kidney disease in a subject in need thereof comprising (a) acquiring a pre-contrast $T_0$ MRI image, (b) injecting an MRI contrast-enhancing substance into the kidney of the subject, (c) obtaining a quantitative-renal-assessment of the subject using the quantitative-renal-assessment system described above, (d) visually displaying the quantitative-renal-assessment, (e) comparing at least one morphological and/or functional parameter from the quantitative-renal-assessment to that of a control subject, and (f) comparing the quantitative renal assessment from the subject with a quantitative renal assessment from a control subject, wherein a difference in at least one morphological and/or functional parameter between the subject and the control subject is indicative of poor prognosis in the subject. In an embodiment, the quantitative organ assessment may be visually displayed.

Also provided is a method for determining a treatment course in a subject with a renal disorder comprising obtaining a quantitative-renal-assessment of the subject by the method for assessing kidney function described above and subsequently determining a treatment course based on the quantitative-renal-assessment.

The quantitative organ assessment system described herein may also be used with organ such as abdomen, brain, breast, heart, liver, lung, neck, pelvis, the musculoskeletal system, ovaries, spine and/or prostate. Accordingly, the quantitative organ assessment system may be used to determine a treatment course in subjects with diseases of the abdomen, brain, breast, heart, liver, lung, neck, pelvis, the musculoskeletal system, ovaries, spine and/or prostate.

In addition, the invention provides a method for obtaining a quantitative-assessment of an organ in a subject in need thereof comprising (a) acquiring a pre-contrast $T_0$ MRI image of the organ in the subject, (b) introducing an MRI contrast-enhancing substance into the subject, (c) obtaining a time series of MRI images stored as a dataset within a computer system, wherein the dataset comprises intensities associated with voxels at each time point in the time series of MRI images, and (d) performing an assessment of the MRI images using a quantitative-organ-assessment component. The component executes on one or more processors of the computer system and generates an assessment of the organ imaged in the time series of MRI images by (i) compressing the dataset to fewer dimensions, (ii) partitioning voxels within the dataset into clusters, each cluster containing voxels with similar time-intensity curves, and (iii) computing functional characteristics and parameters of the organ from aggregate intensity-versus-time characteristics of the voxels within the clusters, thereby obtaining a quantitative-assessment of the organ in the subject.

In an embodiment of the invention, the quantitative organ assessment may be visually displayed, for instance at the discretion of a physician. Global and local parameters may be displayed. These parameters and visualization of these parameters are useful for assessing kidney function in subjects, determining prognosis of kidney disease in a subject and/or determining a treatment course in a subject. In an embodiment, the subject is a patient with renal disorders. Global kidney parameters include but are not limited to split renal function (SRF), differential renal function (DRF), renal transit time (RTT) and/or urinary excretion (UE). Local kidney parameters include but are not limited to time to peak (TTP), impulse response function (IRF), renal blood flow (RBF), plasma flow (PF), glomerular filtration rate (GFR), plasma volume (PV), tubular flow (TF), renal volume of distribution (RVD or VD), mean transit time (MTT) and/or renal perfusion (RP).

As described above, the quantitative organ assessment system described herein may be used with other organs such as abdomen, brain, breast, heart, liver, lung, neck, pelvis, the musculoskeletal system, ovaries, spine and/or prostate. Parameters in these organs that may be used in assessing organ function include but are not limited to blood flow, plasma volume, perfusion and/or impulse response function.

DESCRIPTION OF THE INVENTION

FIGS. 1A-B illustrate a human kidney. In humans, two kidneys serve to carry out a variety of physiological functions, including regulation of electrolytes in the blood, maintenance of blood pH, regulation of blood pressure, filtering of blood to remove wastes, which are excreted into the bladder by the kidneys, re-absorption of water, glucose, amino acids, and other useful substances, and production of various hormones. As shown in FIG. 1A, each kidney has a bean-like shape 102, with a length of approximately 11 to 14 centimeters, a width of approximately six centimeters, and a thickness of approximately three centimeters. A cross-sectional slice through the kidney, shown in FIG. 1B, reveals certain major kidney components. Blood enters the kidney through the renal artery 104 and leaves the kidney through the renal vein 106. Various waste substances are filtered from the blood and collected by the kidney for excretion to the bladder through the ureter 108. The kidney includes an outer cortex 110 and an inner medulla 112. A kidney includes many additional structures, compartments, and components, not shown in FIG. 1B.

FIG. 2 illustrates the process by which a time series of MRIs are acquired from a patient. Initially, at a time point referred to as t=0, a contrast-enhancing substance is injected into the patient as MRI images begin to be produced. In FIG. 2, the t=0 image 202 initially shows no contrast-enhancing substance. Over the course of between 15 and 30 minutes, as shown in the series of images in FIG. 2, the contrast-enhancing substance can be seen to enter the kidney through the renal artery, in image 204, diffuse into the cortex, as shown in image 206, collect in the medulla, as shown in image 208, and eventually leave the kidney by way of the ureter, as shown in image 210. The images shown in FIG. 2 are hypothetical images, and are not intended as a realistic portrayal of the time-dependent concentrations of the contrast-enhancing substance within an actual human kidney.

Figure 3:
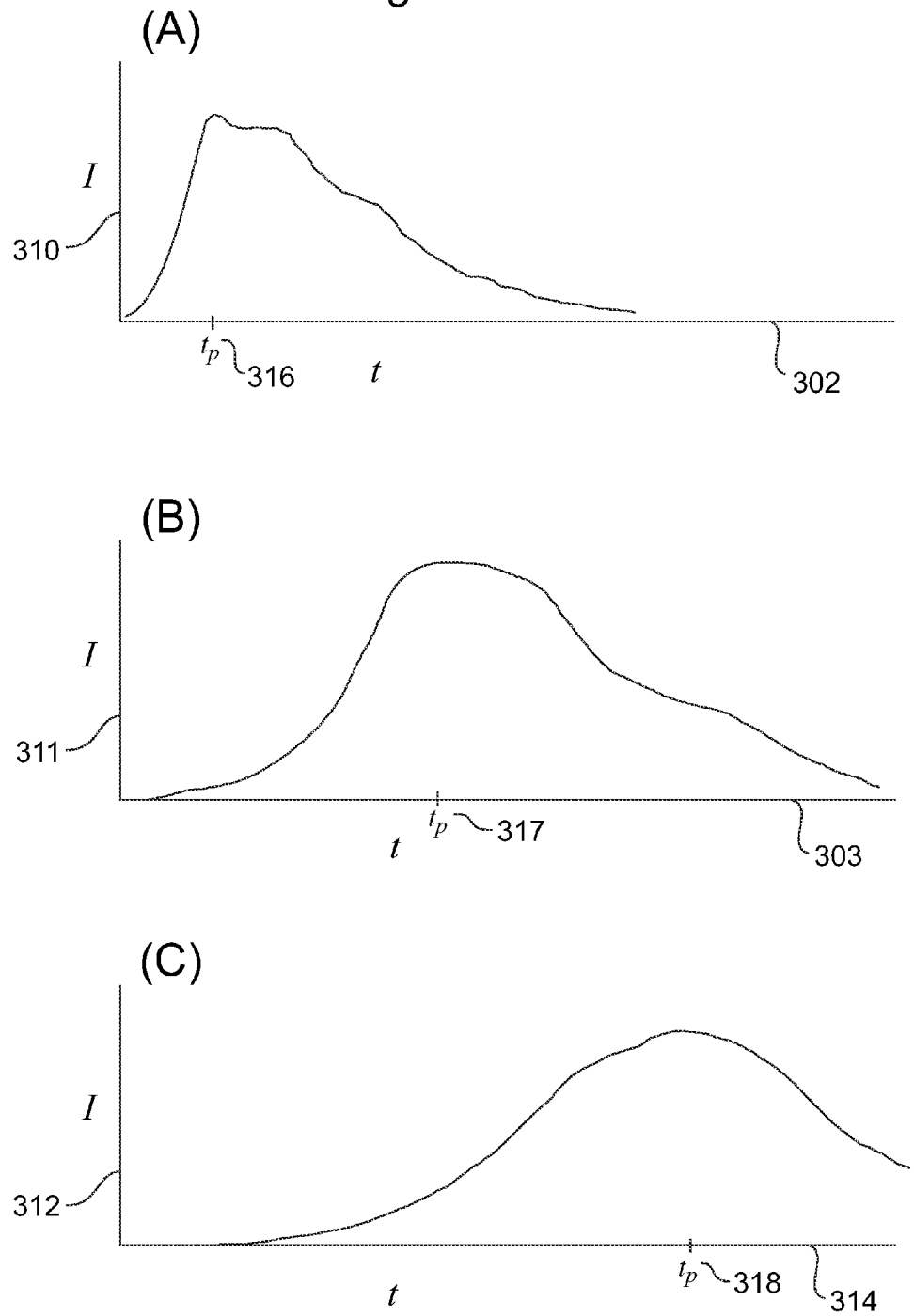
FIGS. 3A-C depict the data collected from an MRI time series.

FIGS. 3A-C illustrate the data collected from an MRI time series. Each of FIGS. 3A-C shows a hypothetical time-intensity curve ("TIC") for a different major compartment of the kidney. FIG. 3A shows the TIC for the renal artery, FIG. 3B shows a hypothetical TIC for the cortex, and FIG. 3C shows a hypothetical TIC for the medulla. All three figures are aligned with one another so that they share a common time axis, represented in each figure by the horizontal axis 302-304. Intensity is plotted with respect to the vertical axes 310-312. The TICs shown in FIGS. 3A-C illustrate how the intensity of pixels within regions corresponding to different kidney compartments rises, as the contrast-enhancing substance flows into the compartment, and then decreases, over time, as the contrast-enhancing substance is eliminated from the compartment. In FIGS. 3A-C, the peak intensity, $t_p$, is shown from each TIC 316-318. The peak intensities occur successively in time for the three different compartments, reflecting the flow of the contrast-enhancing substance initially into the renal artery, then into the cortex, and finally into the medulla, from where the contrast-enhancing substance is eliminated from the kidney. The TIC curves provide the basic information for derivation of many different functional parameters and characteristics, from which abnormal conditions can be determined. Moreover, integration of the volumes of contrast-enhanced voxels can provide information on the volumes of the various components and compartments within the kidney, and thus characterize the morphology of the kidney. A combination of the TIC-derived functional parameters and characteristics and the determined shapes and volumes of kidney compartments and components together constitute a quantitative assessment of the kidney.

Figure 4:
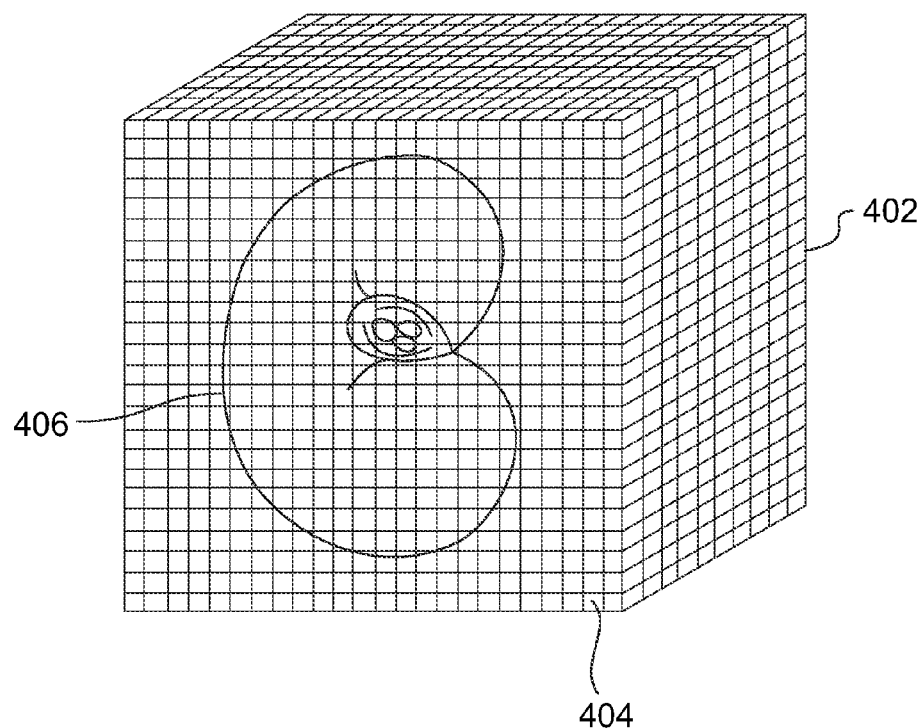
FIG. 4 depicts the nature of the data collected in a single MRI within a time series of MRIs.

FIG. 4 illustrates the nature of the data collected in a single MRI within a time series of MRIs. As shown in FIG. 4, the three-dimensional image constitutes a rectangular volume of voxels 402, each voxel, such as voxel 404, corresponding to the finest granularity of three-dimensional imaging. A voxel is the three-dimensional analog to a pixel in a two-dimensional image. In FIG. 4, the image of the kidney 406 basically constitutes a number of voxels and associated intensities within the rectangular volume of voxels 402.

Figure 5:
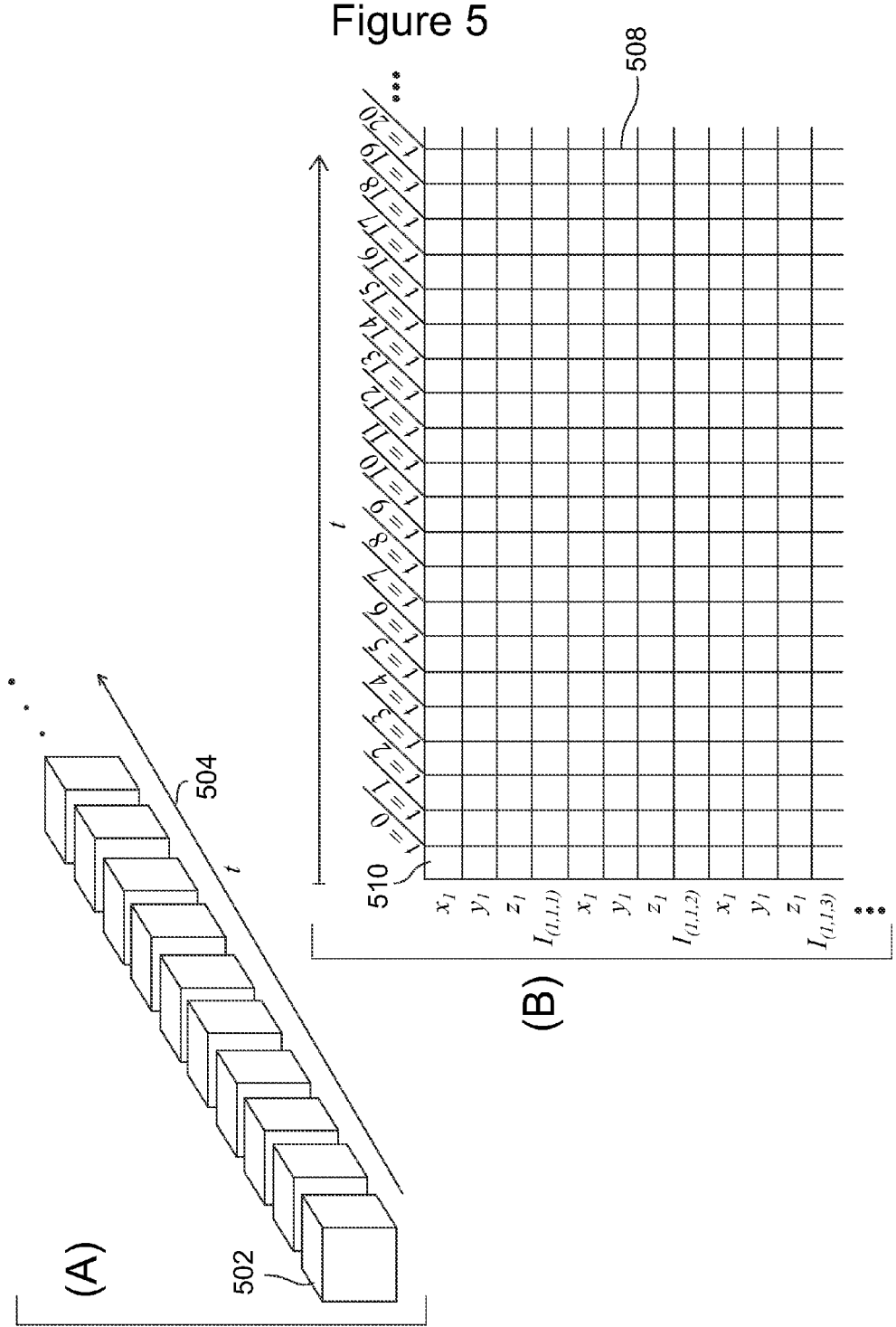
FIGS. 5A-B depicts the enormous amount of data collected in an MRI time series.

FIGS. 5A-B illustrate the enormous amount of data collected in an MRI time series. As shown in FIG. 5A, the MRI time series comprises a sequence of three-dimensional MRI images, such as MRI image 502, acquired over a period of time 504 from about 15 minutes to 30 minutes. Depending on the resolution of the imaging device, each three-dimensional image may contain hundreds of thousands to many millions of voxels. The entire time series of MRIs may include from 30 to several hundred individual three-dimensional MRIs. One can think of the data collected in the MRI time series as a table, as shown in FIG. 5B, with columns, such as column 510, representing each MRI in the time series of MRIs and rows representing the individual data within an MRI. As shown in FIG. 5B, this data may include a Cartesian (x,y,z) coordinate triple for each voxel, as well as the intensity measured for that voxel. Thus, the data matrix 508 may contain from 30 to several hundred columns and many millions of rows. This is a tremendous amount of data to process in order to extract a quantitative renal assessment. Moreover, as noted above, manual visual inspection of a series of 30 to several hundred three-dimensional MRI images is an essentially intractable task, in view of the amount of information in each image and the difficulty in assessing time-dependent changes over a series of such complex three-dimensional images. Method and system embodiments of the present invention are directed to analyzing datasets, such as the dataset illustrated in FIGS. 5A-B, for a time series of MRIs in order to glean the various functional parameters and characteristics and information about kidney morphology that allow diagnosticians to evaluate a patient's kidney and kidney functions. The system is expected to extract more information than human analysis only.

Figure 6:
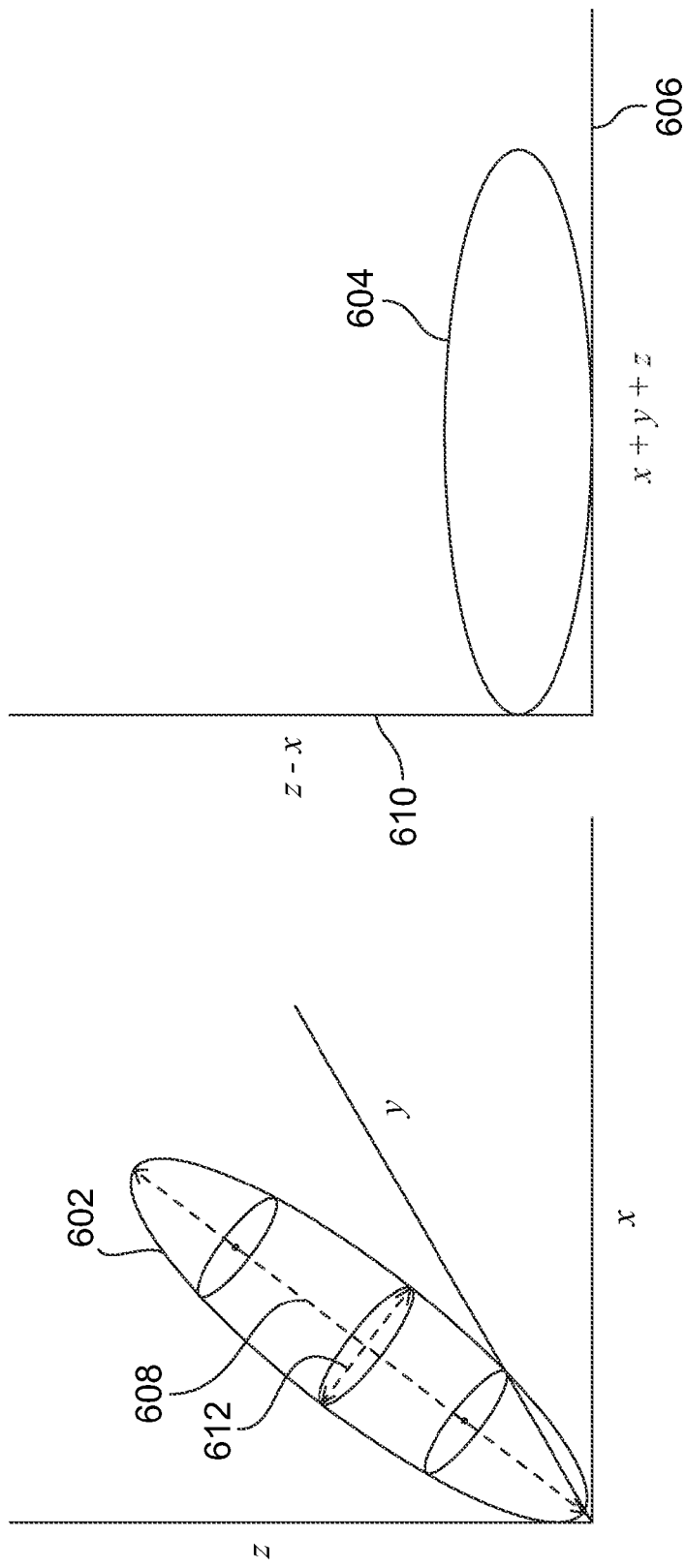
Figure 7:
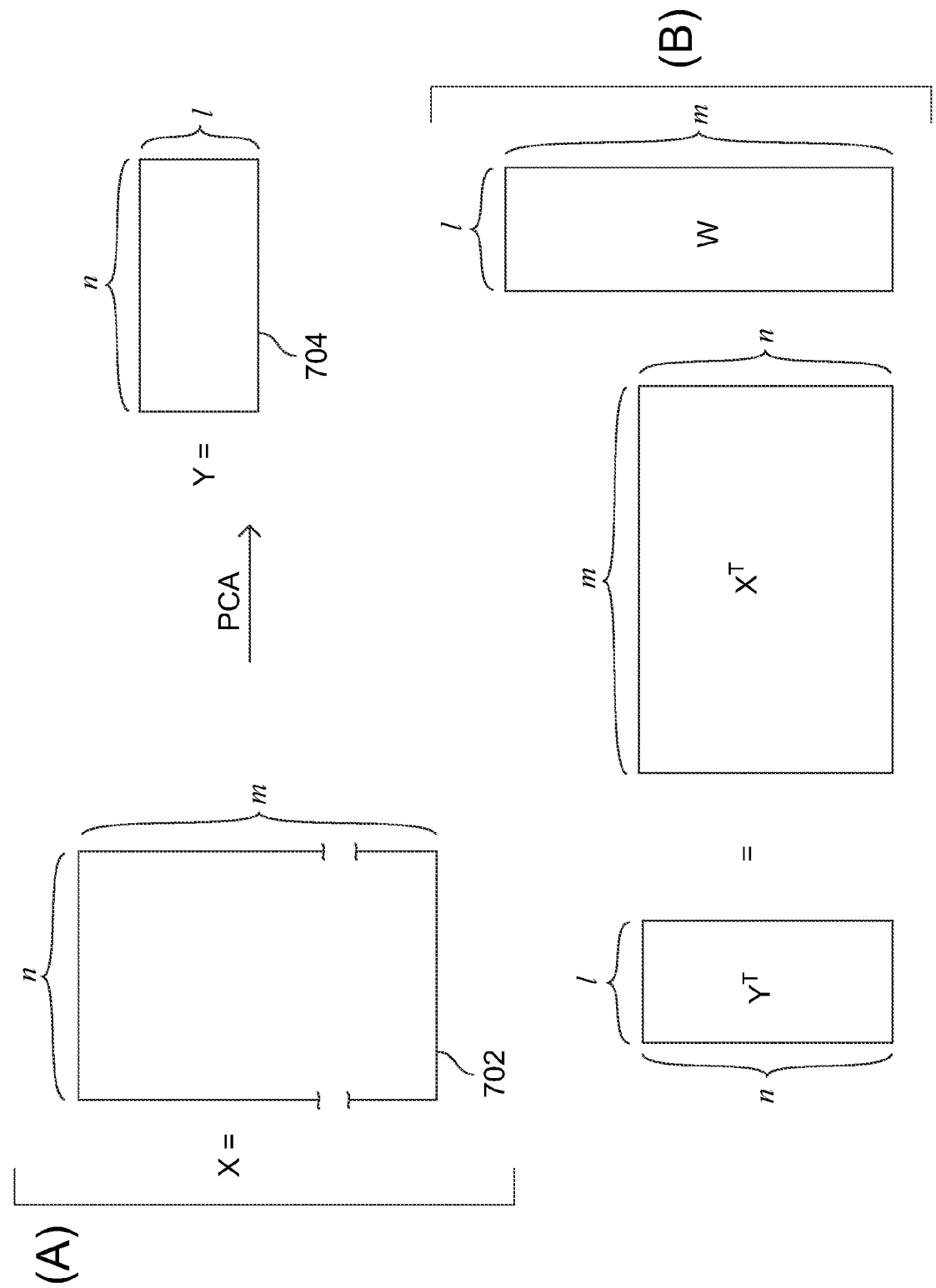

FIGS. 6A-7B illustrate the principal-component-analysis technique that allows for a high-dimension dataset to be compressed into a dataset with lower dimensionality. FIG. 6A shows an elongated, flattened, ellipsoidal data distribution 602 in a three-variable, or three-dimensional, space. The principal-component-analysis method allows this three-dimensional data distribution to be transformed into a two-dimensional projection, 604 in FIG. 6B, which preserves as much useful information as possible. The method chooses a succession of new axes corresponding to independent directions of greatest variation. Thus, a first axis, axis (606 in FIG. 6B), is chosen as the long axis of the ellipsoid distribution (608 in FIG. 6A) and the second axis (610 in FIG. 6B) is chosen as the longest radial axis 612 of the ellipsoid distribution. Although information is lost in the projection, the principal-component-analysis method preserves a greatest amount of useful information associated with the data distribution in the projection. As shown in FIG. 7A, the principal-component-analysis ("PCA") method can be used to transform an m×n dataset matrix X 702 into a lower-dimensional transformed-dataset matrix Y 704 with l<m rows and n columns. Computationally, the PCA method involves finding a basis-vector matrix W in the lower-dimensionality space so that:

X=data set=m×n matrix

W=basis-vectors matrix=m×l matrix

Y=transformed data set=l×n matrix $Y^T = X^T W$ as shown in FIG. 7B.

Embodiments of the present invention employ PCA to compress the enormous amount of data in the time series of MRIs into a transformed dataset of much smaller dimensionality. As it turns out, it is generally the case that, because of the method by which PCA selects basis vectors, most of the useful information within a dataset is preserved in the first handful of dimensions, and transforming a high-dimensional dataset to a low-dimensional dataset acts as an effective noise filter to eliminate small, unimportant variations and allow significant variations to be analyzed.

Figure 8:
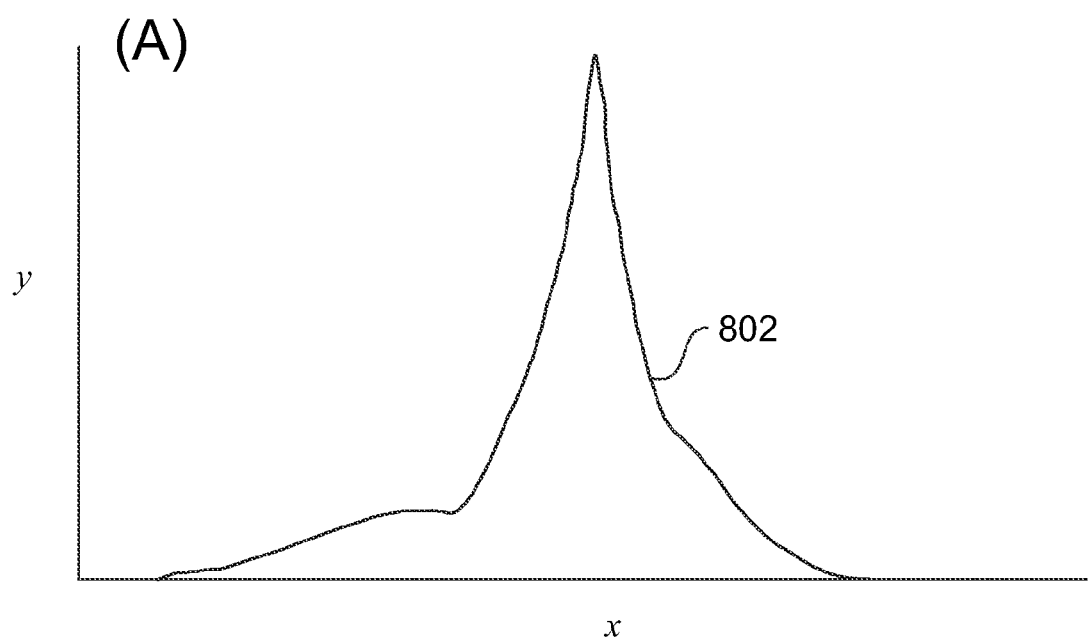
FIGS. 8A-C depict the Gaussian-mixture-model technique for recognizing underlying component distributions within an overall data distribution.
Figure 8:
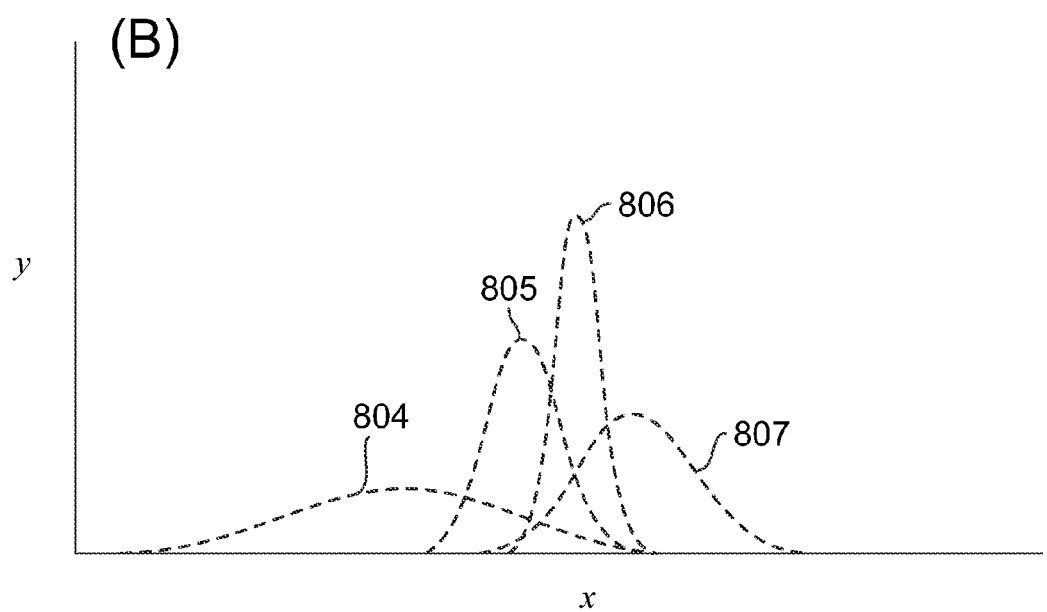
Figure 8:
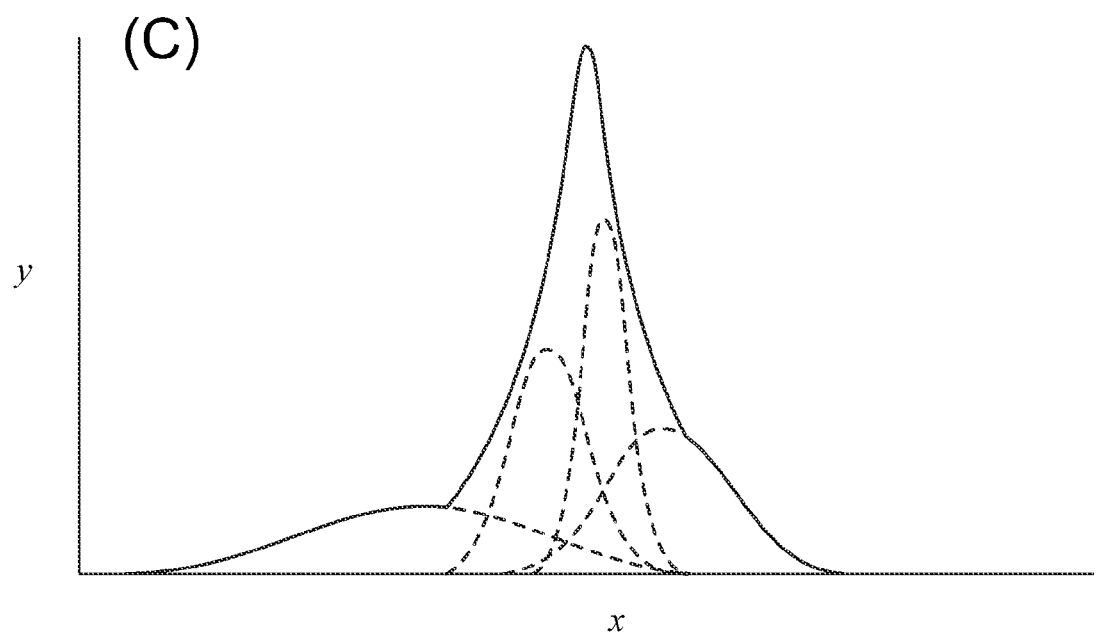

FIGS. 8A-C illustrate the Gaussian-mixture-model technique for recognizing underlying component distributions within an overall data distribution. In FIG. 8A, a data distribution is plotted as a function y=f(x). For example, in a discrete case, y might be the aggregate intensity of a volume of voxels and x might designate an MRI sequence number of an MRI within a time sequence of MRIs. In this example, the function y=f(x) is an average TIC for some portion of a time sequence of MRIs, or volume of voxels. The curve 802 is somewhat complex. The Gaussian mixture model assumes that a curve representing a function of a variable, such as curve 802 in FIG. 8A, is composed from a number of component Gaussian curves. For example, FIG. 8B shows four Gaussian curves 804-807 that, when summed together, as shown in FIG. 8C, produce the curve 802 in FIG. 8A. The finite Gaussian-mixture model approach thus assumes that some function of a random variable X is the sum of a number of component functions of component random variables $Y_i$:

$$f_x(x) = \sum_{i=1}^{n} a_i f_{Y_i}(x)$$

Additionally, a finite parametric Gaussian mixture model further allows each of the component functions to be parameterized:

$$f_x(x) = \sum_{i=1}^{n} a_i f_Y(x, \theta_i)$$

A finite parametric Gaussian-mixture-model approach thus determines the parameters $\theta_i$ and scaling constants $\alpha_i$ for a number n of component random variables $Y_i$ that together produce an observed function of a random variable X, $f_x(x)$.

Figure 9:
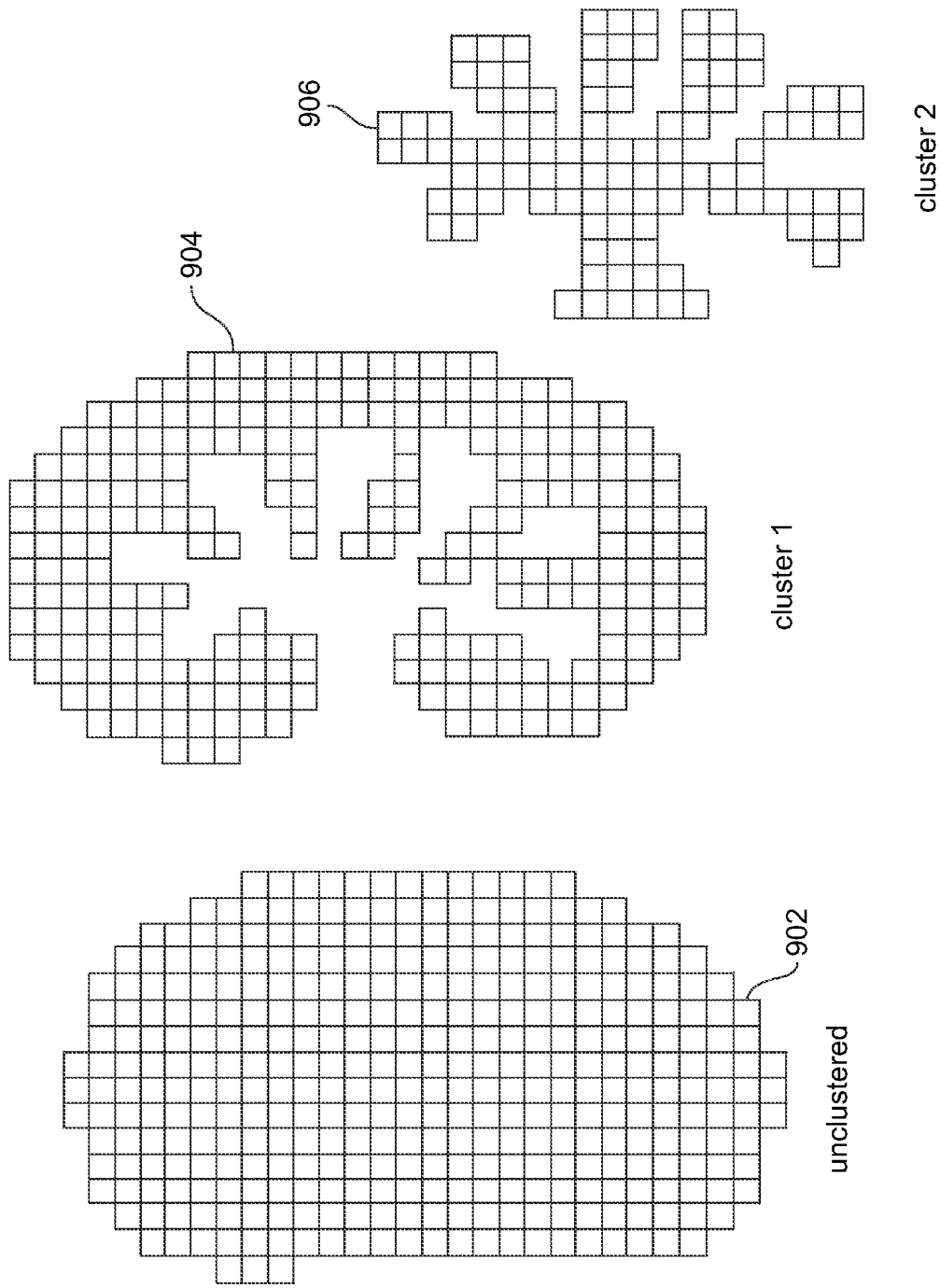
FIG. 9 depicts a clustering process, in two dimensions, that represents one embodiment of the present invention.

Embodiments of the present invention employ a finite Gaussian-mixture model ("FGM") to cluster individual voxels within a volume of voxels corresponding to a kidney into a number of clusters of voxels, each cluster of voxels exhibiting some common, underlying intensity-versus-time behavior within the time sequence of MRIs. Thus, PCA is used to lower the dimensionality of the enormous, high-dimensional dataset represented by the time sequence of MRIs, and FGM is then applied to the lower-dimensional, transformed dataset in order to partition the voxels within a region of the MRIs into clusters of voxels, or components, that exhibit common intensity-versus-time behavior. FIG. 9 illustrates a clustering process, in two dimensions, that represents one embodiment of the present invention. Given that the set of pixels 902 correspond to a kidney within a two-dimensional MRI image, the clustering process can partition these pixels into some number of clusters, such as clusters 904 and 906 in FIG. 9, voxel members of which exhibit similar intensity-versus-time characteristics in a time sequence of MRIs. Because function is related to anatomical location, the clustering approach generally produces clusters corresponding to the major physiological kidney compartments, or components, in the case of normal kidney function. Thus, cluster 904 may correspond to the cortex of the kidney and cluster 906 to the medulla of the kidney.

Figure 10:
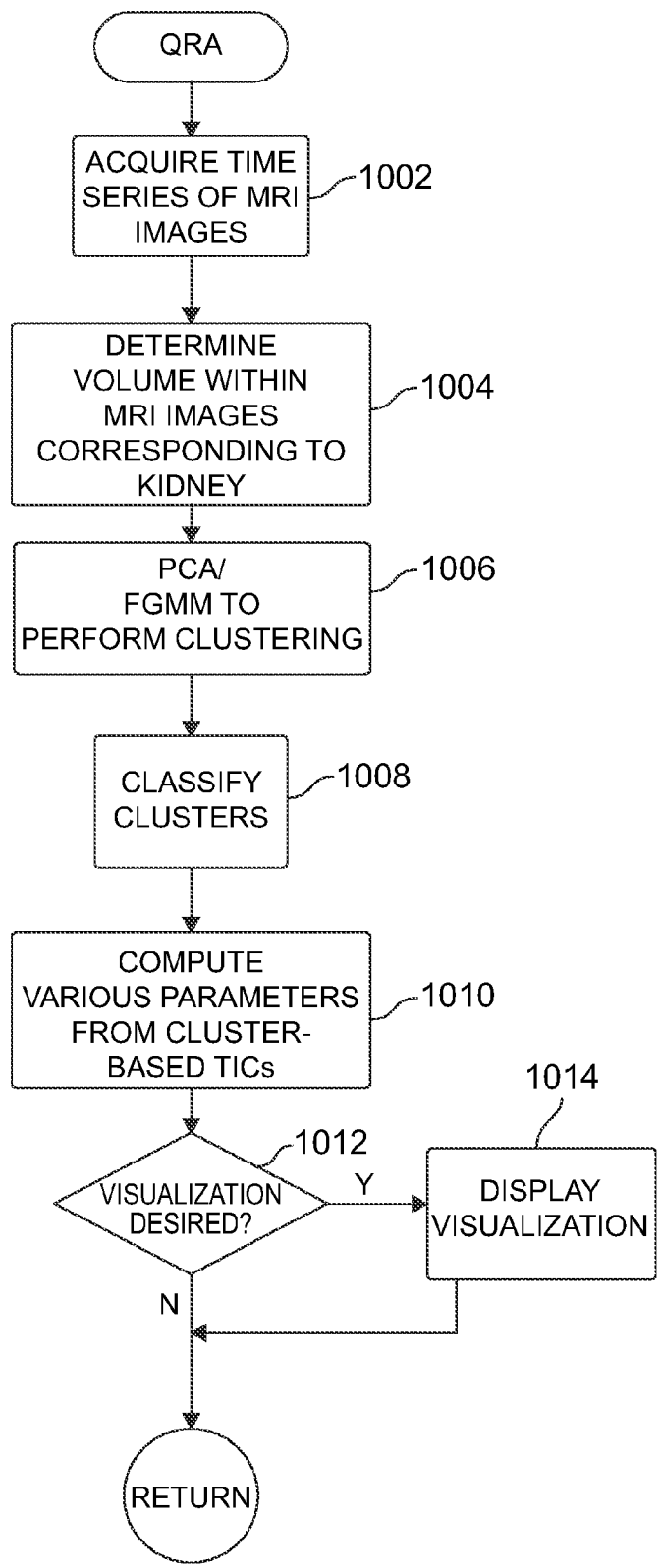
FIG. 10 provides a control-flow diagram of the quantitative-renal-assessment method that represents one embodiment of the present invention.
Figure 11:
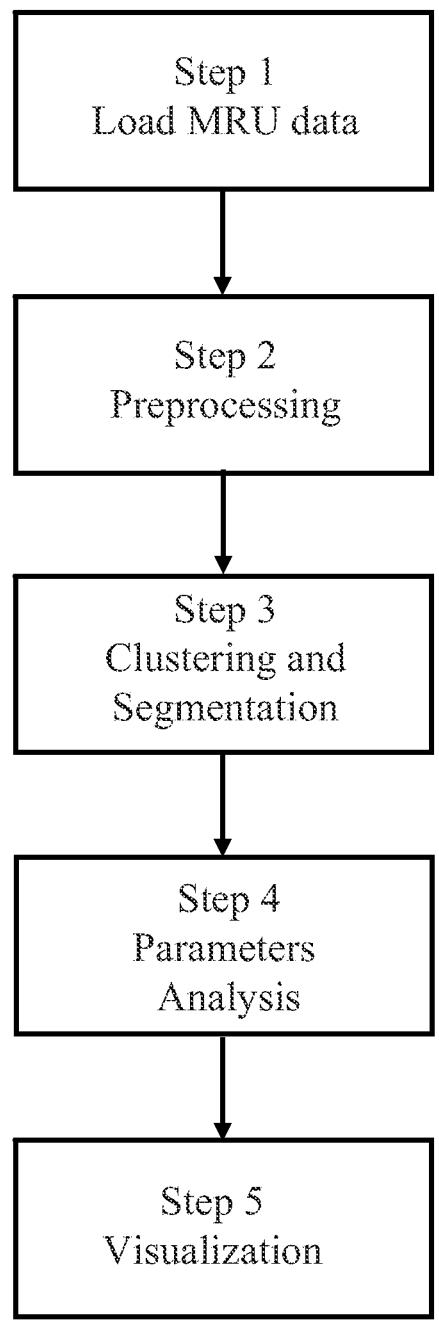
FIG. 11 depicts flow diagrams. (a) shows the main steps in workflow. (b) shows the procedures involved in preprocessing. (c) shows the procedures involved in clustering and segmentation. (d) shows the flow in parameter analysis. (e) shows the flow in visualization.
Figure 11:
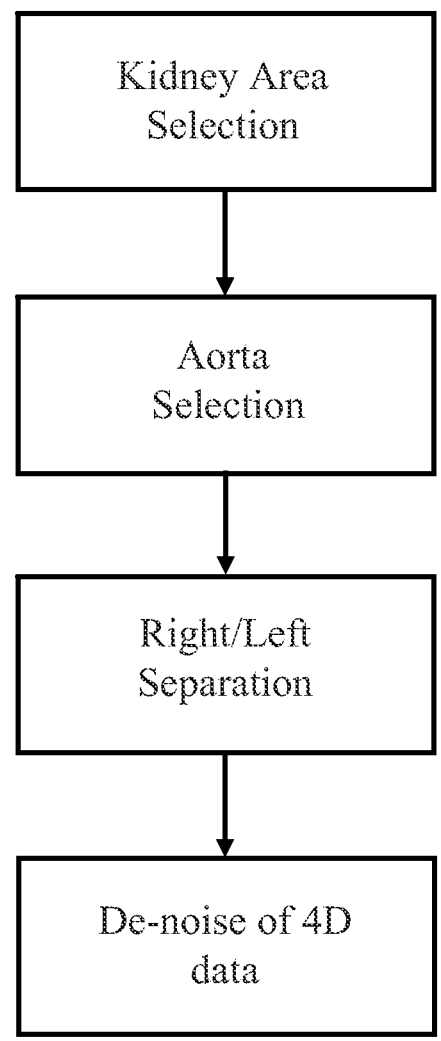
Figure 11:
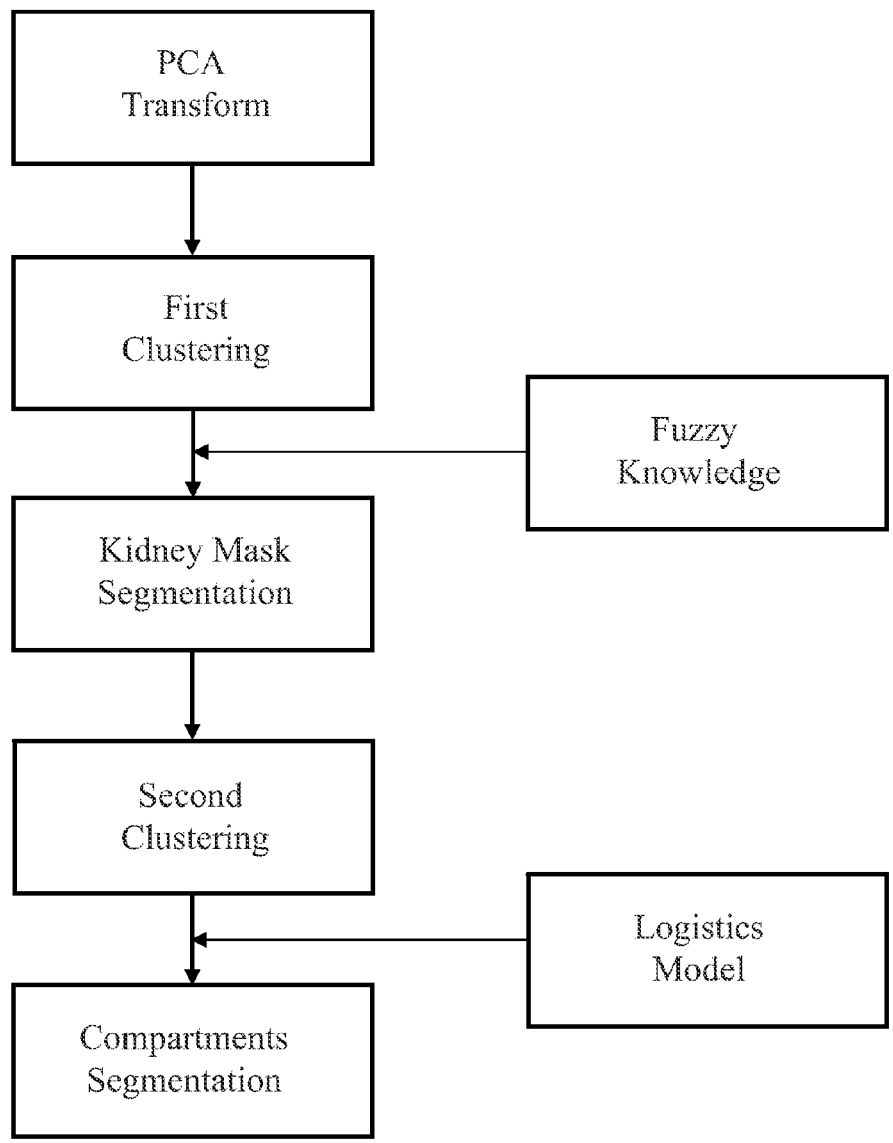
Figure 11:
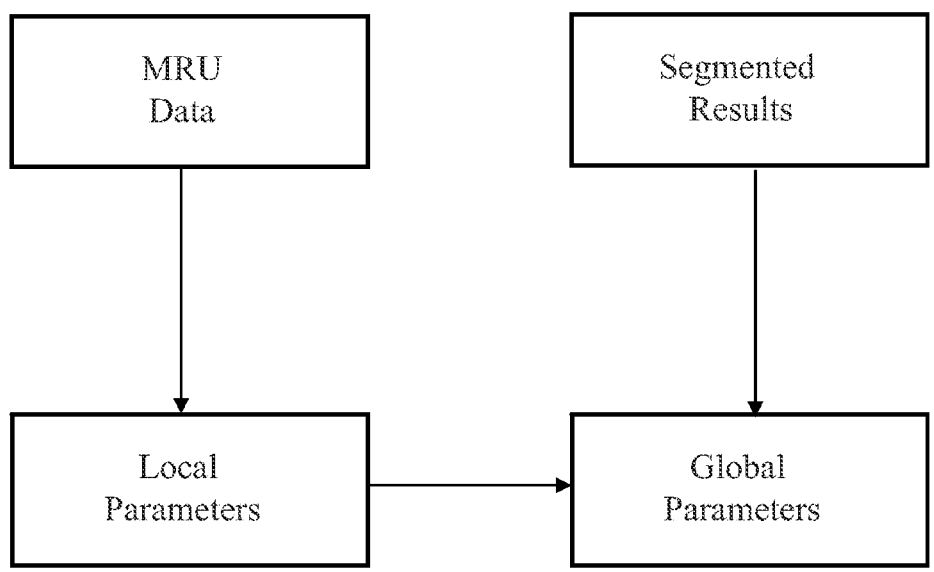
Figure 11:
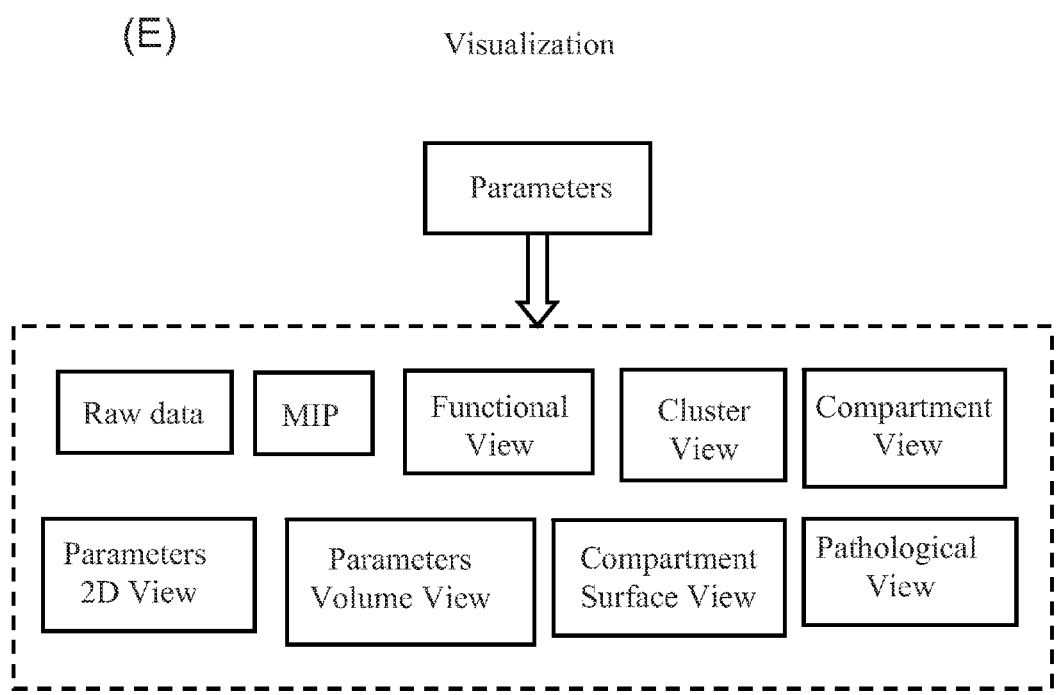

FIG. 10 provides a control-flow diagram of the quantitative-renal-assessment method that represents one embodiment of the present invention. In step 1002, a time series of MRIs is acquired from a patient. Next, in step 1004, the volume of voxels within each of the MRIs corresponding to the kidney to be assessed is determined. This determination can be made manually, by a diagnostician annotating an electronically displayed image, or can be carried out by automated image-analysis methods using various parameters and characteristics gleaned from databases of annotated MRI images. Next, in step 1006, the above-discussed PCA and FGM techniques are used to cluster the voxels within the volume of voxels corresponding to the kidney into a number of clusters, each containing voxels that exhibit similar intensity-versus-time behavior over the time series of MRIs. In step 1008, the clusters may be classified as corresponding to various physiological components and compartments of the kidney. Various methods can be used for classification, as discussed in the article provided in Appendix A. Next, in step 1010, composite TICs for each cluster can be generated and various functional characteristics and parameters for those clusters determined. This step provides a quantitative assessment of kidney function. In addition, the volumes and shape characteristics of the various physiological components and compartments of the kidney can, at this point, be calculated. When visualization is desired, as determined in step 1012, then a composite image can be displayed to a user on an electronic display device, in step 1014. For example, the composite image can show delineations of the various clusters and can use color to indicate the intensity-versus-time characteristics of those clusters. In one embodiment of the present invention, the values for each voxel in the first three dimensions of the PCA-transformed dataset may be mapped to the three dimensions of a color system in order to show the composite image with color corresponding to intensity-versus-time characteristics of the voxels.

Computing Devices

The invention provides a computer system comprising one or more processors wherein the computer system is operable to interface with an MRI machine and executes a software application which (a) obtains a time series of MRI images, (b) stores the MRI images as a dataset within a computer system, wherein the dataset comprises intensities associated with voxels at each time point in the time series of MRI images, and (c) performs an assessment of the MRI images using a quantitative-organ-assessment component. The component generates an assessment of the organ imaged in the time series of MRI images by (i) compressing the dataset to fewer dimensions, (ii) partitioning voxels within the dataset into clusters, each cluster containing voxels with similar time-intensity curves, and (iii) computing functional characteristics and parameters of the organ from aggregate intensity-versus-time characteristics of the voxels within the clusters.

The invention further provides an article comprising one or more machine-readable media storing instructions operable to cause one or more machines to perform operations, the operations comprising (a) obtaining a time series of MRI images, (b) storing the MRI images as a dataset within a computer system, wherein the dataset comprises intensities associated with voxels at each time point in the time series of MRI images, (c) compressing the dataset to fewer dimensions wherein the dataset is obtained from a time series of MRI images and is stored as a dataset, (d) partitioning voxels within the dataset into clusters, each cluster containing voxels with similar time-intensity curves, and (e) computing functional characteristics and parameters of the organ from aggregate intensity-versus-time characteristics of the voxels within the clusters.

In addition, the invention provides a computer readable recording medium including programmed instructions, wherein the instructions, when executed by a computer that includes a display unit for sequentially displaying time-series images, causes the computer to execute operations comprising (a) obtaining a time series of MRI images, (b) storing the MRI images as a dataset within a computer system, wherein the dataset comprises intensities associated with voxels at each time point in the time series of MRI images, (c) compressing the dataset to fewer dimensions wherein the dataset is obtained from a time series of MRI images and is stored as a dataset, (d) partitioning voxels within the dataset into clusters, each cluster containing voxels with similar time-intensity curves, and (e) computing functional characteristics and parameters of the organ from aggregate intensity-versus-time characteristics of the voxels within the clusters.

Figure 21:
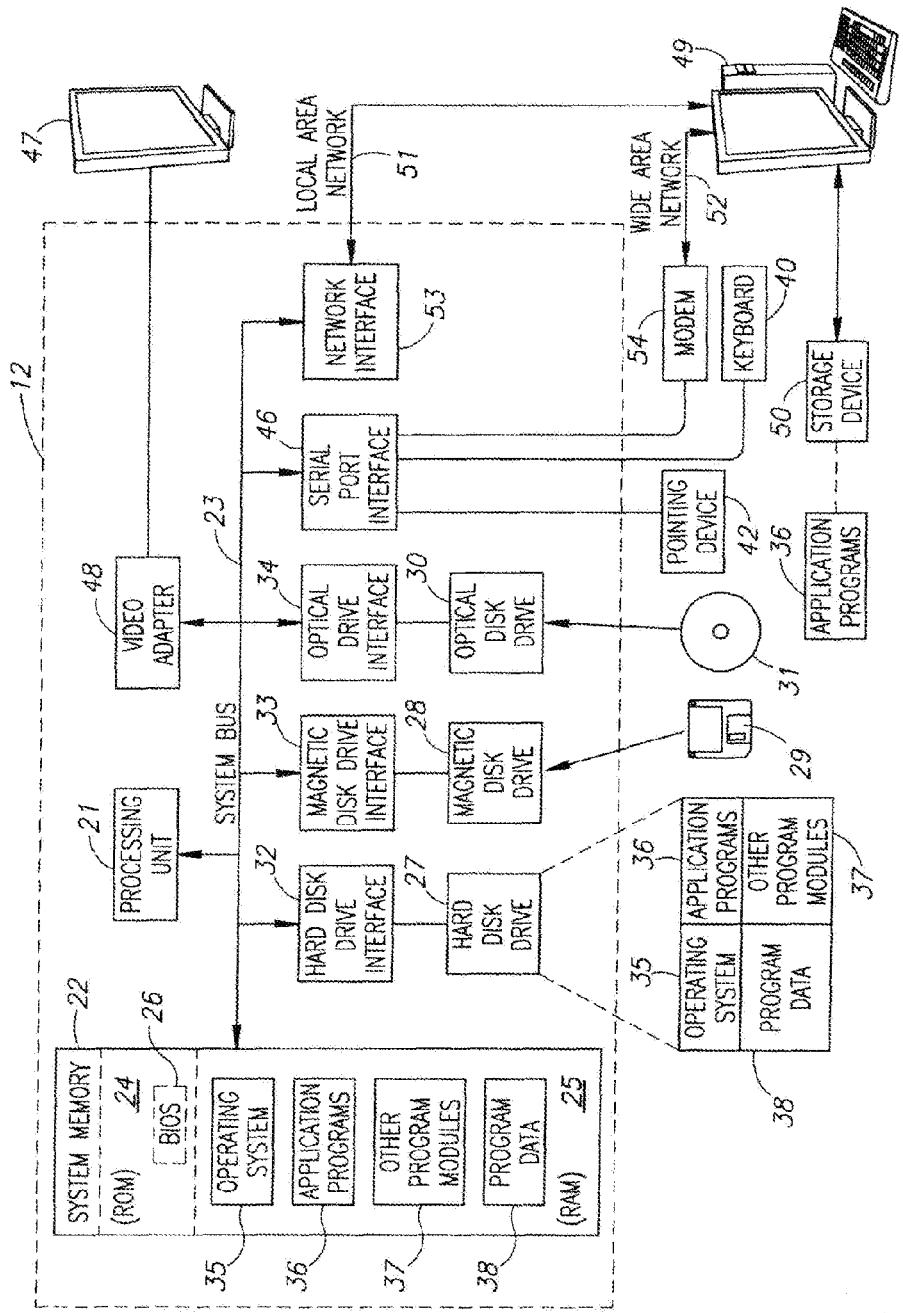
FIG. 21 depicts a diagram of a hardware environment and an operating environment in which the computational-analysis components of the invention may be implemented.

FIG. 21 is a diagram of hardware and an operating environment in conjunction with which implementations of the claimed invention may be practiced. The description of FIG. 21 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multiprocessor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 21 includes a general-purpose computing device in the form of a computing device 12. The claimed invention may each be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer. The system bus 23 may be any of several types of bus structures including a memory bus or memory controller, a peripheral bus, and a local bus using any of a variety of bus architectures. The system memory 21 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feed back game controller).

The monitor 47 may be used to display 3D and/or 2D representations of parameters calculated as claimed. By way of a non-limiting example, the monitor 47 (see FIG. 21) may display 3D and/or 2D visual representations of the DCE-MRI images in form of, for example, parameters calculated as claimed.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 21 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

When executed by one or more processors of the computer system an assessment of a kidney imaged in the time series of MRI images will be generated by (i) compressing the dataset to fewer dimensions, (ii) partitioning voxels within the dataset into clusters, each cluster containing voxels with similar time-intensity curves, and (iii) computing functional characteristics and parameters of the kidney from aggregate intensity-versus-time characteristics of the voxels within the clusters.

Any of the instructions described above, including the instructions of to a) store the MRI images as a dataset within a computer system, wherein the dataset comprises intensities associated with voxels at each time point in the time series of MRI images, (b) compress the dataset to fewer dimensions wherein the dataset is obtained from a time series of MRI images and is stored as a dataset, (c) partition voxels within the dataset into clusters, each cluster containing voxels with similar time-intensity curves, and (d) computing functional characteristics and parameters of the organ from aggregate intensity-versus-time characteristics of the voxels within the clusters, may be stored on one or more non-transitory computer-readable media. The instructions described above are executable by one or more processors (e.g., the processing unit 21) and when executed perform the functions described above.

ADVANTAGES OF THE INVENTION

The invention furthers the practice of evidence based medicine by providing objective analysis of the normal, abnormal and irrelevant. Modern imaging methods yield hundreds of thousands of data points. These data points are analyzed by individuals/humans based on their experience, to eliminate the data points that are not relevant or are noise and to focus on the data that they view as valid. This may result in subjective and sometimes erroneous diagnosis and/or decisionmaking. The process/methodology described and claimed herein insures that the good data and/or useful data are used in diagnosis and/or to make the decisions. The statically-based clustering algorithms described herein reduce the data to similar units or clusters. This mathematically insures that the data used for the practice of evidence based medicine is valid. The statistical analysis described herein provides statistical parameters for defining mathematically significant difference rather than simple human judgment.

EXAMPLES

Example 1

Experimental Methods of the Invention

MRI Protocol

A dynamic MRI with 3D coronal fast GRE sequence was performed on a 1.5 Tesla system. For kidney diagnosis, coils are put near the abdomen area. After a bolus of contrast (Gd-DTPA) was injected, data were acquired with each set of images taking about 30 seconds and the total procedure lasting about 20 minutes. The initial matrix size was 256*256, flip angle is 45, TR range is from 6 to 6.9 ms, and TE range is from 0.83 to 1.27 ms. To keep the linear relationship between the image intensity and the contrast concentration, a dose of the contrast is injected 0.2 mg/kg.

Preprocessing

The target of the preprocessing step is to define an interesting kidney region and de-noise the MRI data. To focus on the relevant area, the user selects a rectangular region that includes the kidney in a maximum intensity projection (MIP) image. To decrease the noise influence, a bilateral filter is adopted for each volume of data in spatial dimensions. Image registration is usually applied to correct movement. Since most of the patients herein are subject to sedation, it isn't a necessary process currently, but can be added if required.

Clustering

In the second stage, the inventors perform the clustering and segmentation for further evaluation. The basic mechanism behind the clustering of dynamic data is to group the voxels with similar TICs. To accomplish this goal, a finite Gaussian mixture model is applied into a transformed principal component feature space of TICs. The statically-based clustering algorithms described herein reduce the data to similar units or clusters. This mathematically insures that the data used for the practice of evidence based medicine is valid. The statistical analysis described herein provides statistical parameters for defining mathematically significant difference rather than simple human judgment.

Principal Component Feature Space

Raw dynamic data often have high dimensions, which increases the computational cost and introduces unnecessary numerical complications. The principal component analysis (PCA) technique is employed for dimension reduction as well as noise suppression in the temporal dimension.

PCA is defined as an orthogonal linear transformation that converts raw dynamic data into a new coordinate space, such that the greatest variance lies along the first coordinate (denoted the first principal component, PC1), and the second greatest variance along the second coordinate (PC2), and so on.

Figure 13:
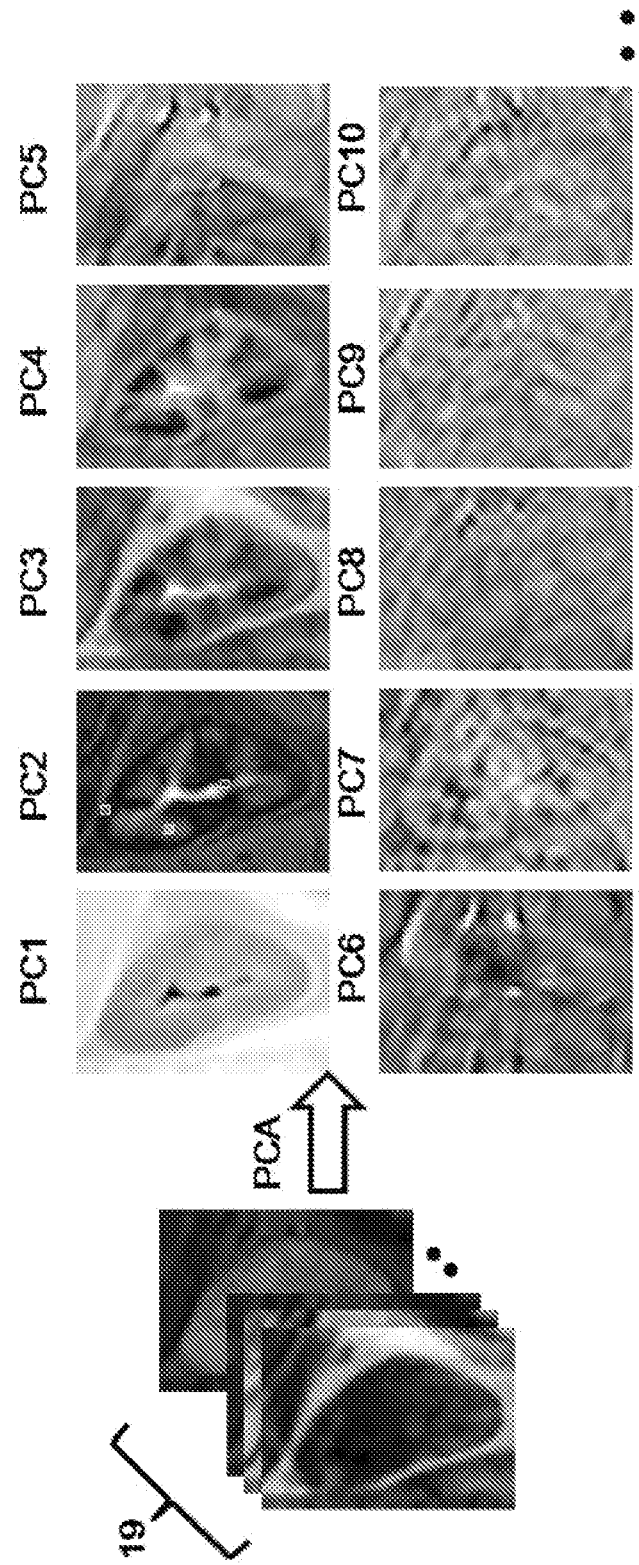
FIG. 13 depicts PCA transformation. The first 10 principal components are displayed of a dynamic slice data with 19 time frames.
Figure 14:
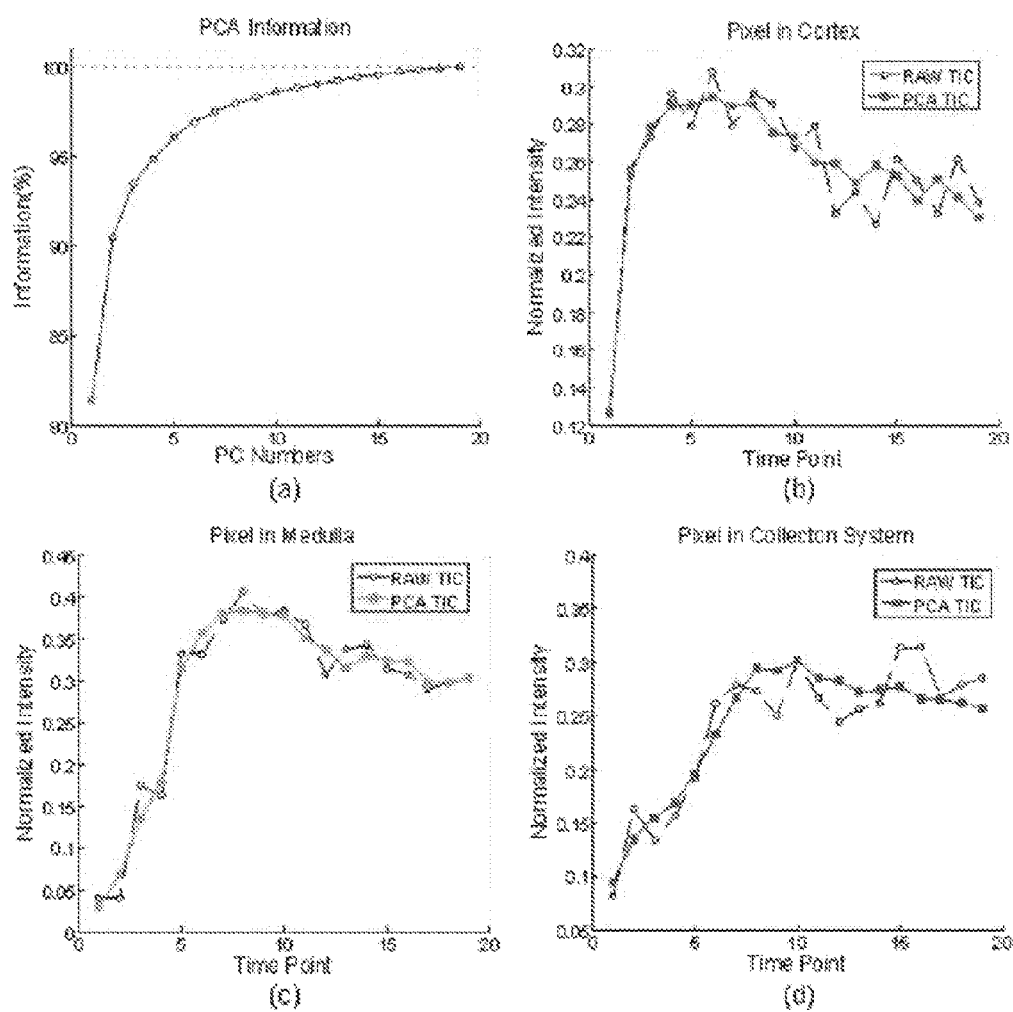
FIG. 14 depicts raw data compared with PCA. (a) Shows that as the number of PCs increase the amount of information included also increases, (b)(c)(d) demonstrate the reconstructed TICs with the first 4 PCs of three pixels in the cortex, medulla and collection system respectively.

From FIG. 13, one can see that useful information is mainly stored in the first 4 PCs and the random noise is kept in the rear later PCs. From the entropy theory, the total information included within increasing PCs is plotted in FIG. 14a. The inventors can find that first PC has already contained about 80% of the total information and the first 4 PCs include more than 95% of the total information. Meanwhile, Compared to the raw TICs, the PCA reconstructed curves remove more noise in the temporal dimension and have a smoother curve defining the intensity trends (FIG. 14c-d). Thus, with the PCA technique, high dimension dynamic data can be transformed into the PCA space with only the first couple of PCs containing most of the useful information.

Finite Gaussian Mixture Model

Gaussian likelihood distribution is a common hypothesis in various medical data processing methods. Here the inventors assume the different clusters are Gaussian distributions in the PCA space, thus the total data composes a finite Gaussian mixture model (FGM) and then the well known expectation maximum (EM) algorithm is used for the clustering.

The FGM utilizes a likelihood function $L(\theta;x,z)$, where $\theta$ is the Gaussian parameter, x is the dynamic data and z represents the labels. To maximize a posteriori estimate (MAP), the EM algorithm iteratively applies the Expectation step and the Maximization step as following.

Expectation-step: $Q(\theta|\theta^{(i)}) = EZ|_{x,\theta(i)}[\log L(\theta;x,Z)]$ Maximization-step: $\theta^{(i+1)} = \mathrm{argmax}_\theta Q(\theta|\theta^{(i)})$ In the Expectation step, the expected value of the likelihood function Q is calculated, and in the Maximization step, the parameters are found to maximize this quantity. When the likelihood function doesn't increase, the iterations will stop and all voxels are grouped into several clusters.

Kidney Mask

Based on clusters, kidney and inner compartments are recognized. Tissues inside the kidney have more complex activities and are easy to confuse with unexpected organs in background, thus the first task is to exclude the kidney mask from the background.

A knowledge-based framework is utilized here to perform the kidney mask recognition. Similar with Brown's work (17), considering of the variance of each feature, the knowledge is described by fuzzy sets. For each feature in the fuzzy logic, a candidate is not completely included or excluded. Instead, a rule is expressed by a fuzzy membership to describe the probability of belonging to target nodes. For the kidney mask, the following features are taken into consideration:

(a) Size: Compared to the background, the size of kidney is expected to be in a certain range, and when the accumulated size of kidney tissues exceeds the range, clusters in the background are probably included.

(b) Centroid: In the cropped data, the kidney is usually located close to the center of the volume. The distance between centroid to the center of each cluster is considered in the knowledge system.

(c) Intensity: The kidney region is usually contrast enhanced, where the intensity is important information used to extract kidney from surrounding structures. The inventors utilized the average intensity in the enhanced phase as the parameter.

(d) Secondary parameters: Some other features derived from the direct parameters are also considered, such as the ratio of intensity to size. In this phenomenon, regions of low intensity and large size have a greater possibility of belonging to the background.

The knowledge above provides enough information to exclude the background from the kidney region. But the set of features from a priori information are not limited to these parameters; more parameters and rules can be added to the knowledge base.

Inner Compartments Recognition

Inner compartments recognition is important for further renal assessment. Compared to the kidney mask, inner compartments have a larger amount of different patterns due to pathological as well as physiological diversities. Although PCA supplies a good compact feature space for most of the DCE-MRI data, it does not work well for further discrimination.

Figure 15:
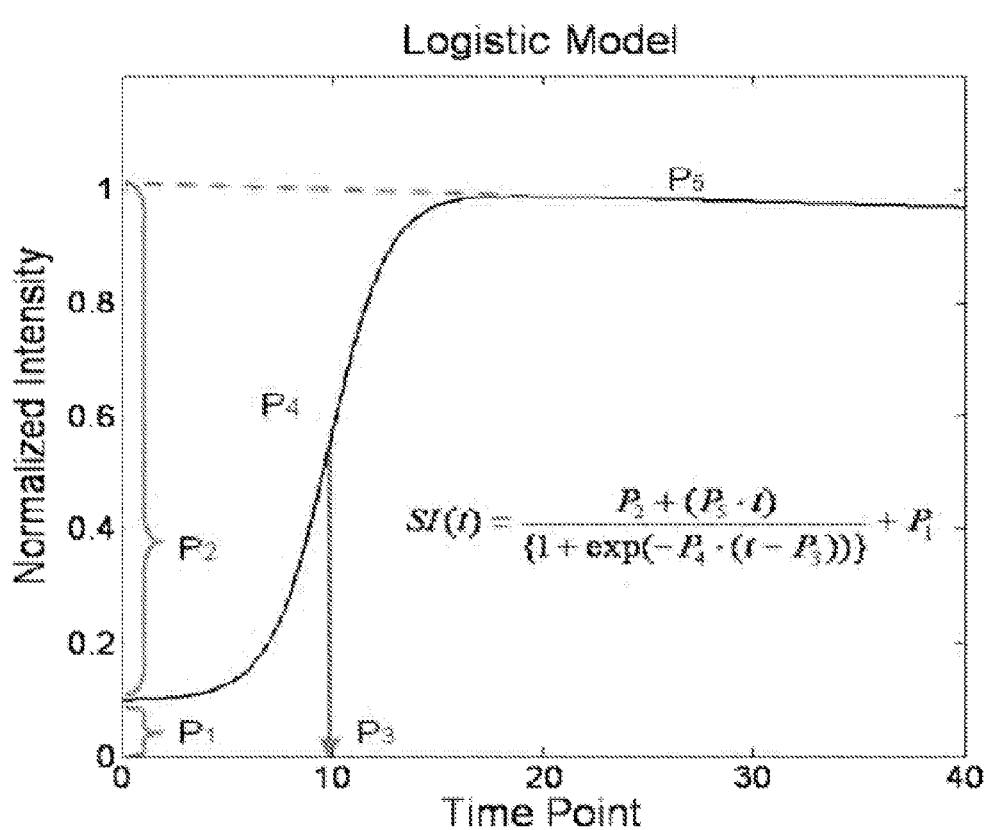
FIG. 15 depicts a logistic model for DCE-MRI analysis.

Considering that inner compartments are physiological different, the inventors tried to distinguish them in a feature space which has physiological meaning. Whereas corresponding physiological meaning to each PC has been discussed in other organs, it is still unavailable for the kidney. To consider such a physiological feature space, a logistic curve model is employed. It describes the signal enhancement in DCE-MRI with five parameters demonstrated in FIG. 15. Where $P_1$ and $P_2$ are related to the magnitude of baseline and peak signal, $P_3$ is the approximate time of the maximum rate of increase, $P_4$ denotes the slope of the enhancement and $P_5$ describe the trends of excretion.

Based on the observation that the kidney area is nearly uniform in the pre-contrast phase, the baseline parameter $P_1$ can be removed to simplify the model. Furthermore, the fitting range can be set to an "expected" range before starting, which will facilitate the fitting process. Thus, the model used is:

$$SI(t) = \frac{P_2 + (P_5 \cdot t)}{\{1 + \exp(-P_4 \cdot (t - P_3))\}}$$

Figure 16:
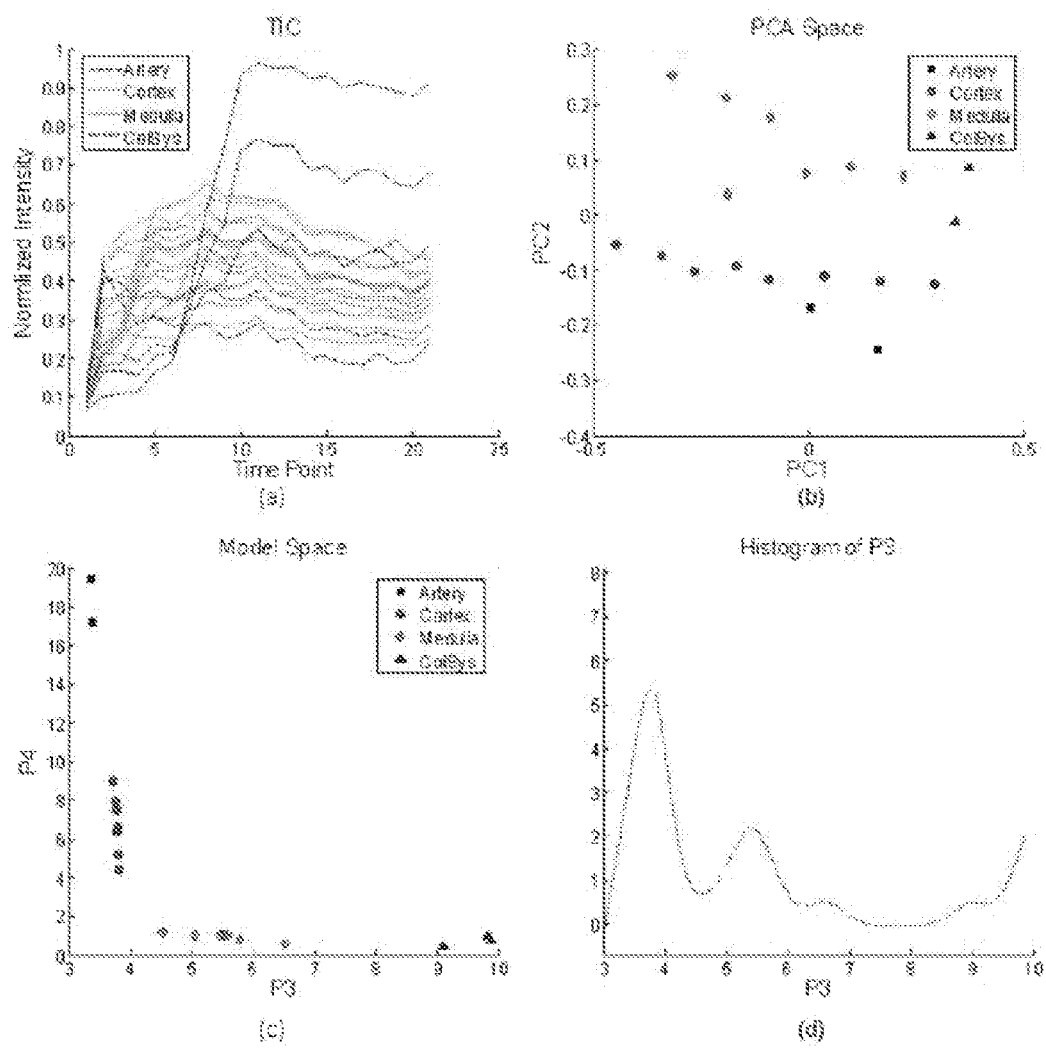
FIG. 16 depicts PCA space vs. logistical model space. (a): the TICs of each cluster. (b): the distribution of each cluster in a PCA space. (c): the distribution of each cluster in a model space. (d): the histogram of $P_3$ distribution in the model space.

With a least squares fitting, 4 parameters are calculated for each cluster. Here two parameters including $P_3$ and $P_4$ were found to work well for further processing, which related to the time to peak (TTP) and renal perfusion (RP) parameters respectively. The inventors' experiments found that logistic model space has a more distinguishable distribution than PCA space as shown in FIG. 16.

Within the model space, a simple linear classifier defined by threshold is employed in this preliminary study. Thus, the criteria for inner compartments separation can be summed as follows:

(a) Cortex and Artery

As shown in FIG. 16c, the cortex is the first region to be contrast enhanced and in the model space all of the clusters are located in a similar region due to their similar TTP ($P_3$) values. Also, their perfusion slope ($P_4$) tends to be higher than other tissues due to physiological mechanisms. The threshold can be set according to the projected $P_3$ histogram (FIG. 16d) by finding the earliest peak.

In TICs (FIG. 16a), it's found that arteries usually have higher peaks in early phases and drop down quickly. Within the logistic model, the artery has a higher $P_4$ and $P_2$, which make it easily distinguishable from the cortex. However, in the current retrospective study, not all arteries could be found due to the low temporal resolution (about 30 seconds) and the peak shape sometimes disappeared.

(b) Medulla and Collecting System

Clusters of medulla and collecting system converge to different centers in the model space. In the histogram of $P_3$ (FIG. 16d), the medulla has a hump next to the cortex, and the collection system is located in the far end. The threshold can be designed by finding the valley between two compartments. Generally, the TTP threshold was set to about 4 minutes after initial enhancement.

Analysis of Parameters

In the third stage, data are analyzed to produce the parameters. As mentioned before, to achieve comprehensive evaluations, the parameters will be calculated both anatomically and functionally. The anatomical parameters are mainly volume sizes and their visual shapes. The functional parameters below are fruitfully defined and discussed in the previous literature (Table. 1). All parameters may be viewed as either global or local. Global parameters are usually a single number for the whole kidney, (i.e. the renal split function), whereas local parameters can be voxel-wise or based on clusters and regions of interest (ROIs). Some local parameters are only active in certain areas. For example, GFR is only suitable for the cortex. All local parameters can be averaged or summarized into global parameters based on certain compartments or on the whole kidney.

TABLE 1

Kidney functional parameters

| | Parameters | Abbre. | Active Area | Definitions | Ref. |
|---|---|---|---|---|---|
| Global | Split/Differential renal function | SRF/ DRF | Kidney | (i) Single renal function is indexed by the product of the area under the TIC curve segment in filtering stage on the parenchymal area and the size of parenchyma. | (2) |
| | | | | (ii) Single renal function is indexed by the size of functional parenchymal. | (21, 22) |
| | Renal transit time | RTT | Kidney | (i) Time from initial enhancement in cortex to the appearance in the collecting system. | (21) |
| | | | | (ii) Time from initial enhancement in cortex to the appearance in ureter. | (12) |
| | Urinary Excretion | UE | Kidney | Decline of the TIC curve segment in excretion stage on the kidney area. | (2) |
| Local | Time To Peak | TTP | Kidney | Time from contrast injection to maximum enhanced | |
| | Impulse Response Function | IRF | Kidney | Deconvolution TIC from the artery input function(AIF) by Fourier transform or truncated SVD method. | (23, 24) |
| | Renal Blood Flow | RBF | Cortex/ medulla | Relate to maximum of the IRF. | (11) |

TABLE 1-continued

Kidney functional parameters

| Parameters | Abbre. | Active Area | Definitions | Ref. |
|---|---|---|---|---|
| Plasma Flow | PF | Cortex/medulla | Similar to RBF. | (25) |
| Glomerular filtration rate | GFR | Cortex | (i) Defined by Patlak plot technique, two compartment model. | (5, 26) |
| | | | (ii) Defined by cortical compartment model. | (6) |
| | | | (iii) Defined by three compartment model. | (7) |
| Plasma volume | PV | Cortex | Intercept of the Patlak plot. | (25) |
| Tubular flow | TF | Cortex | Slope of the Patlak plot. | (25) |
| Renal volume of distribution | RVD/VD | Cortex/medulla | Relate to time integral of IRF. | (11, 25) |
| Mean transit time | MTT | Cortex/medulla | Ratio of RVD by RBF. | (11, 25) |
| Renal perfusion | RP | Cortex | (i) Ratio of the fractional PV by the vascular MTT. | (27) |
| | | | (ii) Defined by up-slope model. | (28) |
| | | | (iii) The maximum up-slope of the kidney curve divided by the peak of aortic bolus. | (29) |

More parameters can be derived for further reference, such as statistical parameters of clusters or ROIs (histogram, variance), or derivative parameters from TIC curves ($1^{st}$ derivative, $2^{nd}$ derivative), which can be added according to the research requirements.

Visualization

Visualization is a key task for clinicians and a 3D result is especially helpful to surgeons. In the inventors' method, data are displayed in various ways. All the calculated parameters provide a 2D and 3D visualization. Examples are displayed in FIG. 19. Most visualization results are intuitive and two of them are specifically described here.

(a) Functional View

The functional view shows the time series in a multi-channel color image, which has been used in MR Mammography before (30). The basic idea is to set the first 3 PCs to the RGB channel respectively, and then show the functional activity with color intensity (FIG. 19c).

(b) Pathological View

Figure 19:
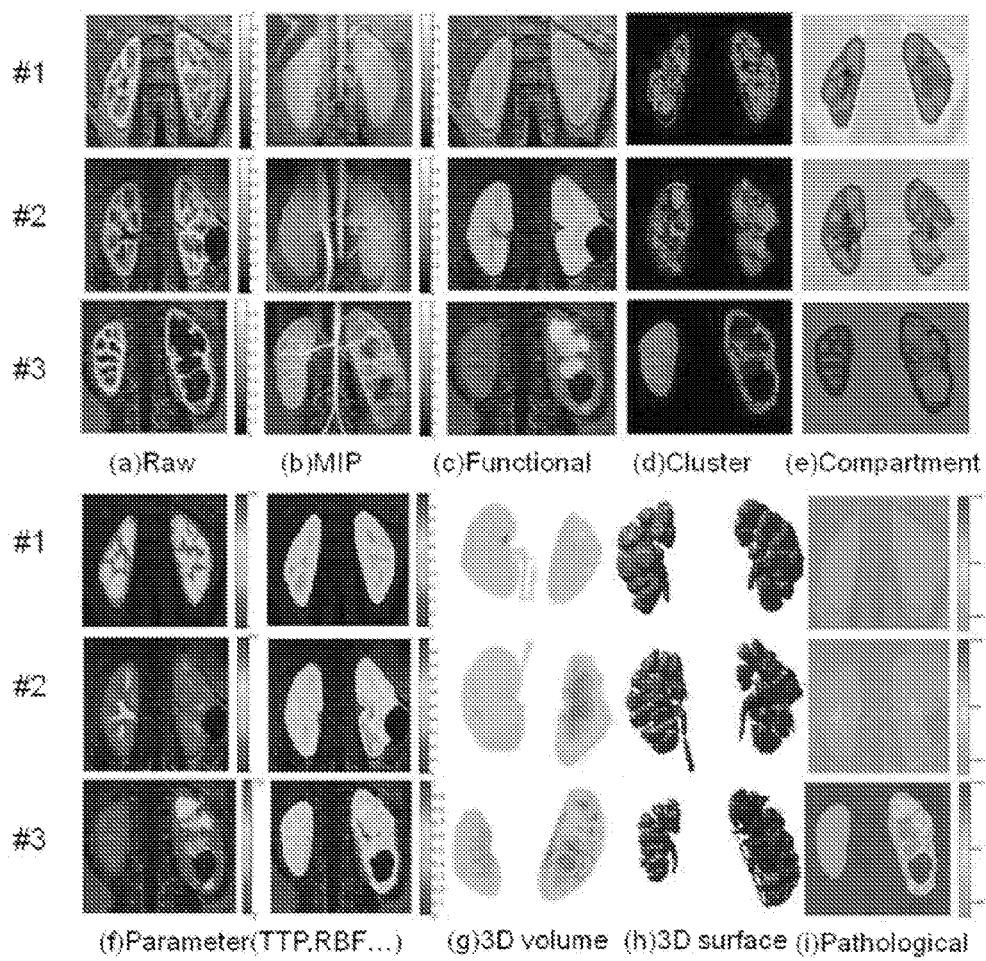
FIG. 19 depicts visualization examples.

A pathological view is defined here to show the activity difference between target and reference regions. The reference regions represent the healthy tissue and can be selected manually or calculated from the average for each compartment. The pathological view will give a score for each tissue which represents the difference between the selected tissue and healthy tissue. The score is defined by the cosine equation (Equ. 2) between the target and reference TICs. Results close to 1 indicate a healthy region and are marked with a green color while red colored regions are potentially diseased areas (FIG. 19).

Example 2

Results

Digital Phantom

To test the capacity of dealing with noise, a 4D digital phantom is designed for the experiments herein, which is spatially composed of three inner compartments, and has time series activities in the fourth (temporal) dimension. The average time series activities are calculated from real data and used as typical TICs for each compartment.

Fifty trials were performed by adding Gaussian white noise, with variance increasing from $10^{-5}$ to 1, to the digital phantom. Simultaneously, the signal to noise ratio (SNR) decreased from 56.5 to 0.7. The SNR is defined as ratio of the average signal and RMS (root mean square) noise in the early enhanced phase.

Figure 17:
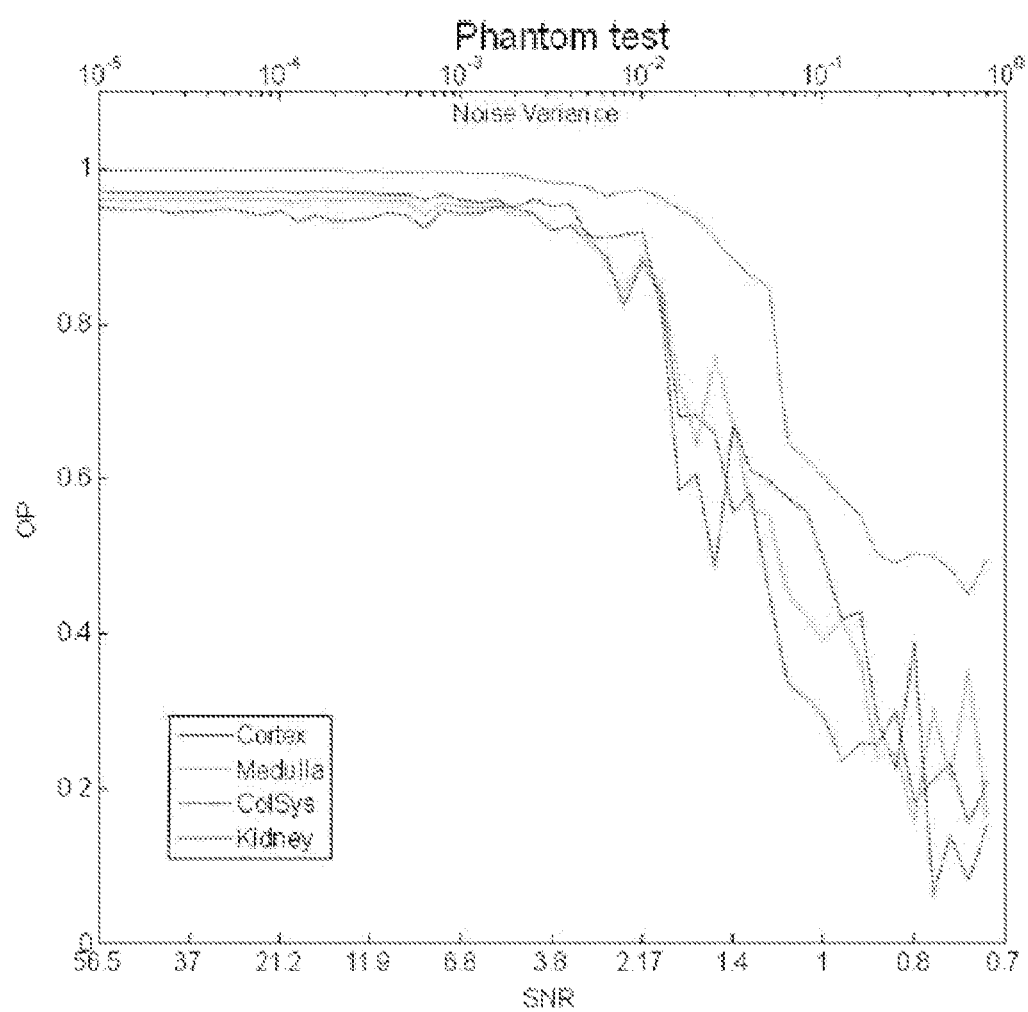
FIG. 17 depicts phantom evaluation with decreasing SNR.

The inventors compare the segmented results of the method ($R_1$) with the ground truth ($R_2$) for kidney masks as well as inner compartments. The overlap percent (OP) is defined as Equ. 1 for the similarity measurement and the results are displayed in FIG. 17.

$$OP = \frac{1}{2}\left(\frac{|R_1 \cap R_2|}{|R_1|} + \frac{|R_1 \cap R_2|}{|R_2|}\right) \quad (1)$$

From the experiments, the inventors found that the method works well when SNR is higher than 3.8 (for kidney masks OP approaches 1, and for inner compartments OPs are greater than 0.9).

Figure 12:
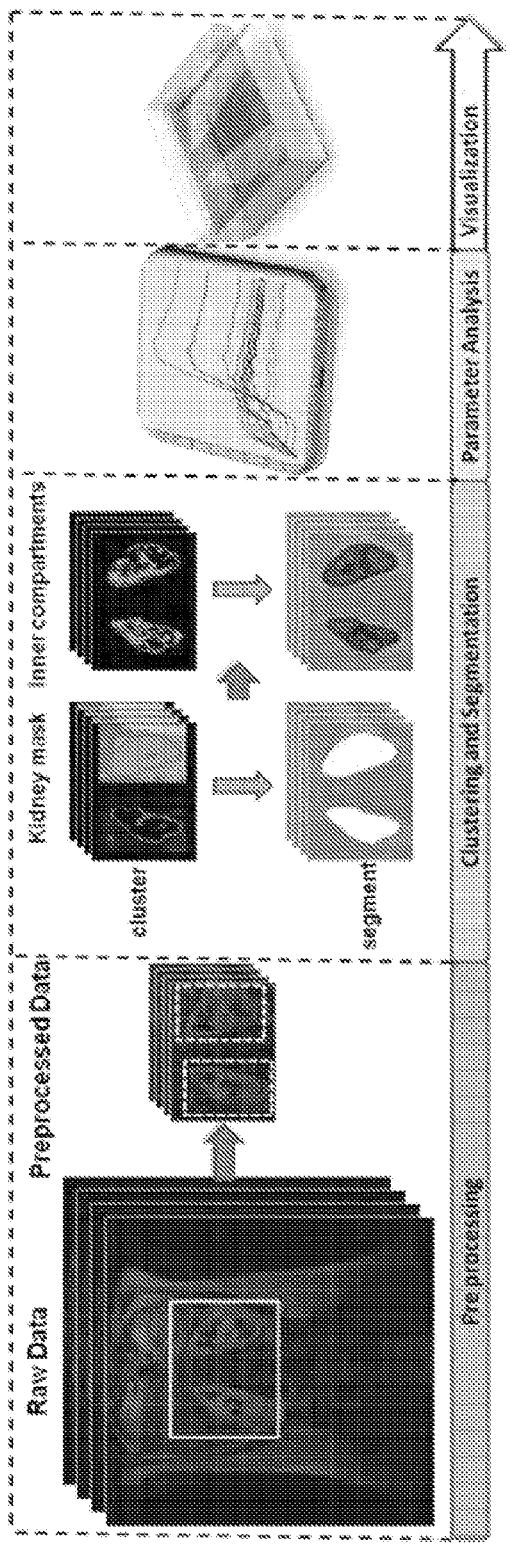
FIG. 12 depicts the 4 major stages of the post processing workflow, which includes the preprocessing, clustering and segmentation, parameter analysis and visualization.

Clinic Data 22 kidneys from a pediatric clinic database of kidney data were investigated. The data with obvious artifacts were excluded. Each kidney underwent the complete post processing as shown in FIG. 12. Both anatomical and functional parameters with the manual processed reference for each kidney were compared. For the automatic method, 18 of the 22 tests were calculated automatically and 4 kidneys needed minor user interaction of the cluster selection mainly due to the pathological disorders. For the manual reference, a typical slice in the middle of each kidney that included all the three compartments was selected in order to minimize error segmentation that often occurs in the outer slices.

For morphological similarity, the same overlap percent measurement (Equ. 1) is used. For functional validation, the average TICs of each compartment are compared for their similarity. The cosine metric is adopted to measure the angle between two TIC vectors. The statistical results are listed in Table 2.

TABLE 2

Statistical similarities between automatic and manual results

|  | Compartments | Mean | STD |
|---|---|---|---|
| Morphological | Kidney | 0.9587 | 0.0118 |
|  | cortex | 0.8136 | 0.0387 |
|  | medulla | 0.7995 | 0.0424 |
|  | colsys | 0.8700 | 0.0632 |
| Functional TIC | Kidney | 0.9999 | <0.001 |
|  | cortex | 0.9998 | <0.001 |
|  | medulla | 0.9998 | <0.001 |
|  | colsys | 0.9996 | <0.001 |

$$similarity_{TIC} = \cos(\theta) = \frac{TIC_1 \cdot TIC_2}{\|TIC_1\|\|TIC_2\|} \quad (2)$$

Figure 18:
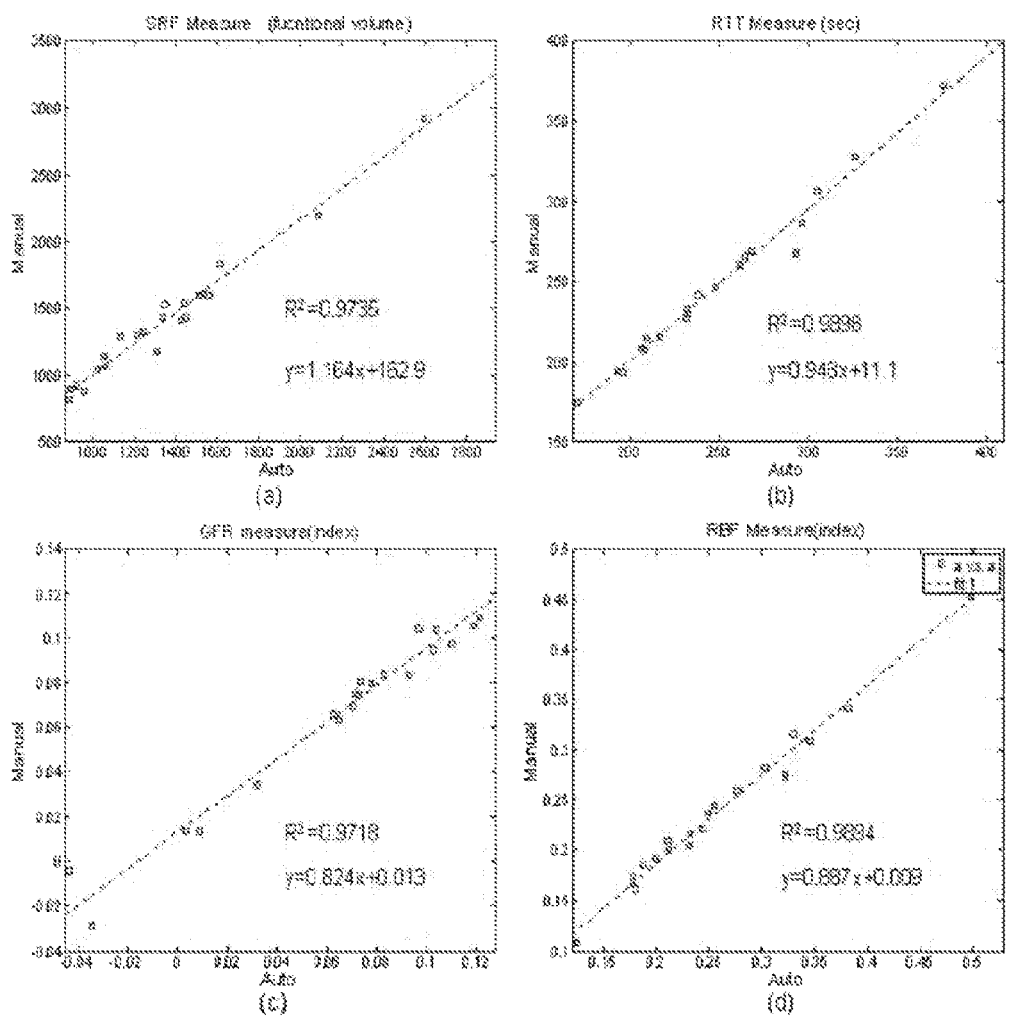
FIG. 18 depicts a correlation between the functional parameters estimated by the automatic and manual methods.

Along with the TICs, 4 functional parameters including SRF (defined in 2), RTT(21), GFR(5) and RBF(11) are selected for tests, which rely on both the anatomical compartments and TICs. Correlations coefficients are calculated between automatic and manual results with a confidence bound 95%. The results are displayed in FIG. 18.

Visualization

Various visualization techniques are supplied in the inventors' method. Three typical examples are displayed including a patient with healthy kidneys (patient1), a patient with a cyst in the left kidney (patient2) and a patient with hydronephrosis caused by an ureteropelvic junction obstruction (UPJ) on left kidney (patient3).

In FIG. 19 (a)-(e) show the slice view of raw, MIP, functional, cluster and compartment views. For each functional parameter, both 2D slice view (f) and a 3D volume view (g) is provided. In the 3D volume view, the alpha threshold can be adjusted for inner observation of the kidney. For the anatomical view, a 3D surface view is provided for a flexible observation as well (h). The pathological views are listed in (i), where parameters are scaled between green and red to indicate being normal or abnormal.

Tool Overview

Figure 20:
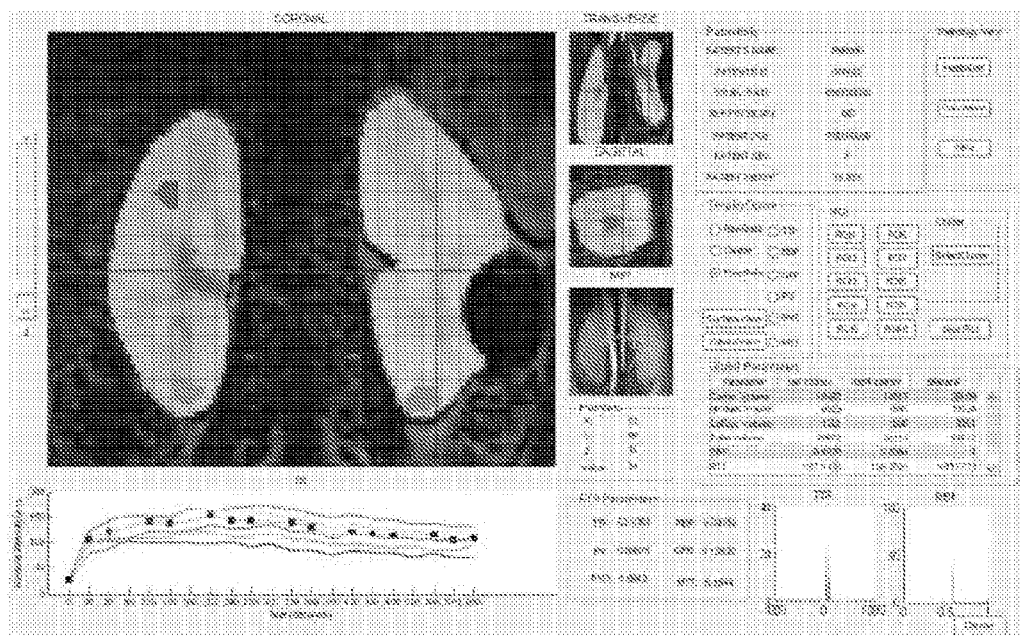
FIG. 20 depicts visualization GUI.

The method is implemented as a research tool in Matlab (Mathworks, Natick, Mass.) platform with mex files written in C++ and OpenGL support for 3D visualization. Following the workflow (FIG. 12), the tool mainly includes four modules including preprocessing, segmentation, analysis and visualization. In the analysis modules, the inventors implemented most of the parameters in Table 1 as an optional selection for comparative research. The GUI of the visualization module is shown in FIG. 20, where the TICs of the clusters are displated at the bottom and the global parameters are shown on the right panel. The traditional ROI operation is retained along with the cluster selection function. In FIG. 20, multiple ROIs are circled in the functional images of three different views and the local parameters statistics from the ROIs are listed on the bottom with their histograms plotted to the right.

Example 3

Discussion

The inventors have demonstrated a processing workflow based on clusters of dynamic kidney MRI data. The clusters group voxels with similar TICs in a 3D manner and supply a more precise visual description to allow faster clinical insight. Based on the clusters, automatic methods for kidney masking and compartmental identification are also designed, which is important for both anatomical and functional analysis. To provide a more intuitive visualization for quantification parameters, multiple options and interactions are supplied.

In the inventors' method some assumptions are made during the processing. First, for the inner compartments, three tissues are taken into account including cortex, medulla and collection system. Although there are more than three compartments in the state-of-the-art kidney model, for the current imaging protocol only these three partitions were practical in the instant study. For example, the more advanced multi-compartment model includes tubule level analysis, which in practice is challenging to analyze when using current DCE-MRI data. With further developed imaging techniques, the inventors will be able to look more inside of compartments.

With this assumption, there are three compartments in the volume data. But for some severely disordered kidneys with large hydronephrosis or complete lack of function, especially in cases where cortex is very thin, the method does not work well. Also, limitations of the automatic analysis still exist for clearly damaged kidneys. This limitation occurs because the common knowledge used in the kidney mask segmentation is not suitable, and in such cases more user intervention is required.

In this post processing, the number of clusters is important for target identification in each step. In the first clustering step for the kidney mask, if the number is set too small (such as 2 or 3), the kidney tissues will not separated from background or nearby organs. However, if the number is set too large, each cluster will shrink and the knowledge from each cluster (such as size, position) will have more variance. The inventors' experiments have found that from 4 to 8 is a good range for kidney mask segmentation. The cluster number inside the kidney mask is usually related to the user's intentions and their desired detail level. From a radiologist's point of view, about 20 clusters are usually enough to high clinically important physiological differences inside the kidney. It also worked well for the compartmental identification in the inventors' experiments. Another parameters is the number of PCs in the PCA analysis, the inventors' experiments found that the first 5 PCs are usually enough for accurate processing because they contain more than 95% of the useful dynamic information.

As described in the section 2.5, only simple thresholds are set for the inner compartments. However, there is more potential to distinguish different compartments and gather more useful information. For example, statistical learning processes can be adopted, and with enough samples and based on the supervised knowledge, the inner compartments identification could be more precise and reliable. Also, artificial neural networks (31) can be taken into account for the different kidney diseases based on the cluster's TIC, resulting in the analysis being performed in a more intelligent way.

Currently the knowledge for kidney mask recognition works well on the instant experiments, but for pediatric research each feature has more variance than in adults. Thus an improved knowledge system still needs to be established dependent on age, gender, and ethnic group.

For the parameters, most current values are calculated by model free methods, which produce relative or semi-quantitative values. In the next step, more attention will be paid to absolute parameter calculations. Also, the results are mainly validated by manual operations within the MRI modality.

More validations are needed within the different modalities and the next step is to design a study with extensive clinical input.

Appendix A includes a pseudocode implementation of one embodiment of the present invention.

REFERENCES

1. Rohrschneider W K, Haufe S, Wiesel M, et al. Functional and morphologic evaluation of congenital urinary tract dilatation by using combined static-dynamic MR urography: findings in kidneys with a single collecting system. Radiology 2002: 224:683-694.
2. Wiltrud K R, Sabine H, Manfred W, et al. Functional and morphologic evaluation of congenital urinary tract dilatation by using combined static-dynamic mr urography: findings in kidneys with a single collecting system. Radiology: 2002: 224:683-694.
3. Coulam C H, Bouley D M, Sommer F G. Measurement of renal volumes with contrast enhanced MRI. J Magn Reson Imaging 2002; 15:174-9.
4. Tofts P S, Brix G, Buckley D L, Evelhoch J L, Henderson E, Knopp M V, et al. Estimating kinetic parameters from dynamic contrast enhanced T1-w MRI of a diffusible tracer: standardized quantities and symbols. J Magn Reson Imaging 1999: 10:223-32.
5. Hackstein N, Heckrodt J, Rau W S. Measurement of single-kidney glomerular filtration rate using a contrast-enhanced dynamic gradient-echo sequence and the Rutland-Patlak plot technique. J Magn Reson Imaging 2003: 18:714-725.
6. Annet L, Hermoye L, Peeters F, Jamar F, Dehoux J P, Van Beers B E. Glomerular filtration rate: assessment with dynamic contrast-enhanced MRI and a cortical-compartment model in the rabbit kidney. J Magn Reson Imaging. 2004; 20:843-849.
7. Lee V S, Rusinek H, Bokacheva L, et al. Renal function measurements from MR renography and a simplified multicompartmental model. Am J Physiol Renal Physiol 2007; 292: 1548-1559.
8. Buckley D L, Shurrab A E, Cheung C M, Jones A P, Mamtora H, Kalra P A. Measurement of single kidney function using dynamic contrast-enhanced MRI: comparison of two models in human subjects. J Magn Reson Imaging. 2006: 24:1117-1123.
9. Gandy S J, Sudarshan T A, Sheppard D G, Allan L C, McLeay T B, Houston J G. Dynamic MRI contrast enhancement of renal cortex: a functional assessment of renovascular disease in patients with renal artery stenosis. J Magn Reson Imaging 2003: 18: 461-466.
10. Michaely H J, Herrmann K A, Kramer H, Dietrich O, Laub G, Reiser M F, Schoenberg S O. High-Resolution Renal MRA: Comparison of Image Quality and Vessel Depiction with Different Parallel Imaging Acceleration Factors. J Magn Reson Imaging 2006: 1: 95-100.
11. Dujardin M, Sourbron S, Luypaert R, et al. Quantification of renal perfusion and function on a voxel-by-voxel basis: a feasibility study. Magn Reson Med 2005: 54:841-849.
12. Jones R A, Easley K, Little S B, et al. Dynamic contrastenhanced MR urography in the evaluation of pediatric hydronephrosis: part 1 functional assessment. AJR 2005: 185:1598-1607
13. Tomasi C, Manduchi R. Bilateral Filtering for Gray and Color Images. Proceedings of the IEEE International Conference on Computer Vision 1998.
14. Baudouin D S, Iosif A M, Sébastien R, Isky G, Chrit M, Nicolas G. Improvement of MRI-functional measurement with automatic movement correction in native and transplanted kidneys. J Magn Reson Imaging 2008: 28:4:970-8.
15. Hachamovitch R, Shufelt C. Statistical analysis of medical data-Part I: Univerariable analysis. Journal of Nuclear Cardiology 2000: 7:5:146-152.
16. Dempster A P, Laird N M, Rubin D B. Maximum Likelihood from Incomplete Data via the EM Algorithm. Journal of the Royal Statistical Society 1997: 39: 1: 1-38.
17. Brown M S, McNitt-Gray M F, Mankovich N J, Goldin J G, Hiller J, Wilson L S, Aberle D R. Method for segmenting chest CT image data using an anatomical model: preliminary results. IEEE Trans Med Imaging 1997: 16:6: 828-39.
18. Zadeh L A. Fuzzy sets. Information and control 1965: 8:338-353.
19. Erez E, Dania B, Edna F H, Fredrick K, Kevin J K, Hadassa D. Principal component analysis of breast DCE-MRI adjusted with a model-based method. J Magn Reson Imaging 2009: 30:989-98.
20. Moate P J, Dougherty L, Schnall M D, Landis R J, Boston R C. A modified logistic model to describe gadolinium kinetics in breast tumors. Magn Reson Imaging 2004: 22:467-473.
21. J. Damien G S, Marcos, R P, Richard A J, et al. MR imaging of kidneys: functional evaluation using f-15 perfusion imaging. Pediatr Radiol 2003: 33:293-304.
22. Richard A. Jones1, Brian Schmotzer2, Stephen B. Little3 and J. Damien Grattan-Smith1, MRU post-processing, Pediatric Radiology 2008: 38:18-27.
23. Rempp K A, Brix G, Wenz F, Becker C R, Guckel F, Lorenz W J. Quantification of regional cerebral blood flow and volume with dynamic susceptibility contrast-enhanced MR imaging. Radiology 1994: 193:637-641.
24. Murase K, Yamazaki Y, Miyazaki S. Deconvolution analysis of dynamic contrast-enhanced data based on singular value decomposition optimized by generalized cross validation. Magn Reson Med Sci 2004; 3:165-175.
25. Michaely H J, Sourbron S, Dietrich O, Attenberger U, Reiser M F, Schoenberg S O. Functional renal mr imaging: an overview. Abdom Imaging 2006: 32:6:758-771.
26. Patlak C S, Blasberg R G, Fenstermacher J D. Graphical evaluation of blood-to-brain transfer constants from multiple-time uptake data. J Cereb Blood Flow Metab 1983: 3:1-7.
27. Hermoye L, Annet L, Lemmerling Ph, et al. Calculation of the renal perfusion and glomerular filtration rate from the renal impulse response obtained with MRI. Magn Reson Med: 2004: 51:5:1017-25.
28. Montet X, Ivancevic M K, Belenger J, Jorge-Costa M, Pochon S, Pechere A, Terrier F, Vallee J P. Noninvasive measurement of absolute renal perfusion by contrast medium-enhanced magnetic resonance imaging. Invest Radiol 2003: 38:584-592
29. Michoux N, Vallée J P, Pechère-Bertschi A, Montet X, Buehler L, Van Beers B E. Analysis of contrast-enhanced MR images to assess renal function, Magn Reson Mater Phy 2006: 19:4:167-79.
30. Erez E, Hadassa D. Model-based and model-free parametric analysis of breast dynamic-contrast-enhanced MRI. NMR in Biomedicine 2007: 22:1:40-53.
31. Lucht R, Delorme S, Brix G. Neural network-based segmentation of dynamic MR mammographic images. Magn Reson Imaging 2002: 20:147-154.

Although the present invention has been described in terms of particular embodiments, it is not intended that the invention be limited to these embodiments. Modifications will be apparent to those skilled in the art. For example, the quantitative-renal-assessment systems that represent embodiments of the present invention can be implemented on many different types of computer systems in many different ways, by varying any of the many different implementation parameters, including programming language, operating system, control structures, data structures, modular organization, and other such implementation parameters. Although the above discussion focuses on imaging the morphology and function of the kidney, alternative embodiments of the present invention may be directed to other internal organs and tissues, with suitable changes in image-acquisition methods and parameters and derivations of functional characteristics.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the claims below and their equivalents.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

APPENDIX A

PSEUDOCODE IMPLEMENTATION

```
%preprocessing
%select image in the folder
[filename,pathname]=uigetfile('*.*','choose image in 1st te');
fileFullPath=strcat(pathname,filename);
%read parameters of MRU data
totalFileNum=str2num(get(edit_TotalFileNum,'string'));
sliceNum=str2num(get(edit_SliceNum,'string'));
sliceBegin=str2num(get(edit_SliceBegin,'string'));
sliceEnd=str2num(get(edit_SliceEnd,'string'));
precontrastNum=str2num(get(edit_Precontrast,'string'));
fileFullPath= fileFullPath;
%load dicom images
LoadSliceDCM(totalFileNum,sliceNum,sliceBegin,sliceEnd,filePrefix
,patientID,precontrastNum);
%Region selection
axes(axes_xy);
imagesc(imgXY);
axes(axes_yz);
imagesc(imgYZ);
h_xy = imrect;
h_yz = imrect;
h_left = imrect;
h_right = imrect;
h_aorta = imrect;
pos_xy = round(getPosition(h_xy));
```

APPENDIX A-continued

PSEUDOCODE IMPLEMENTATION

```
pos_yz = round(getPosition(h_yz));
pos_left = round(getPosition(h_left));
pos_right = round(getPosition(h_right));
pos_aorta = round(getPosition(h_aorta));
SaveRegionInfo(pos_xy,pos_yz,pos_left,pos_right,pos_aorta);
%calculate the average AIF
CalAIF(kidneyData,pos_aorta);
%de-noise
Load(kidney_data);
for timepoint=1:t
%for                left               kidney
kidSmoothDataL(:,:,:,i)=Denoise3D(kidney_left,'bilateral');
%for right kidney
kidSmoothDataR(:,:,:,i)=Denoise3D(kidney_right 'bilateral');
end
%save denoised data
SaveSmoothData( );
%clustering and segmentation
Load_smooth_kidney_data( );
%PCA transform
TIC=reshape(kidneyData);
TIC=TIC−TIC(:,1)*ones(1,t);
[COEFF,SCORE,latent,tsquare] = PCATransform(TIC);
PCs=SCORE(:,1:PCnum);
%first clustering
%get cluster num
clusterNum1=str2num(get(handles.edit_ClusterNum1,'String'));
%cluster by EM algorithm
Cluster1=EM_MRF(PCs,clusterNum1);
%calculate info for each cluster
For i=1:clusterNum1
index=find(u==i);
size_array(i)=size(index,1);
centroid_array(i,:)=mean(pos(index,:),1);
centriod_dis_array(i)=norm(centriod_array(i,:)−center_pos);
TICmean(i,:)=(mean(TIC(index,:),1));
End
TICmeanmean=mean(TICmean,2);
inten_size=TICmeanmean./size_array;
%recognition by fuzzy knowledge
renalIndex=FindKidneyFuzzy(TICmeanmean,size_array,inten_size,
centriod_dis_array);
%save the kidney mask
kidneyMask=FindBiggestConnectRegion(renalIndex);
Save(kidneyMask);
%second clustering
%get cluster num
clusterNum2=str2num(get(handles.edit_ClusterNum2,'String'));
%cluster by EM algorithm
Cluster2=EM_MRF(PCs,clusterNum2);
%calculate mean TICs for each cluster
for i=1:clusterNum2
index=find(Cluster2==i);
clusterTICs(i,:)=mean(kidneyData(index,:),1);
end
%transform to new space by logistic model
for i=1:clusterNum2
ParameterLog(I,:)=LogTransform(clusterTICs(i,:));
end
%recognize inner compartments
[corInd,medInd,colInd]=RecogInner(ParameterLog);
%save the inner mask
Save(InnerMask);
%Parameters Analysis
%save the optional method selection of parameters
TTP_string=get(get(handles.uipanel_TTP,'SelectedObject'),'String');
RBF_string=get(get(handles.uipanel_RBF,'SelectedObject'),'String');
GFR_string=get(get(handles.uipanel_GFR,'SelectedObject'),'String');
PV_string=get(get(handles.uipanel_PV,'SelectedObject'),'String');
RVD_string=get(get(handles.uipanel_RVD,'SelectedObject'),'String');
MTT_string=get(get(handles.uipanel_MTT,'SelectedObject'),'String');
SRF_string=get(get(handles.uipanel_SRF,'SelectedObject'),'String');
Save(ParaConfig);
%Load data
Load(AIF);
Load(kidneyMask);
Load(innerMask);
Load(ParaConfig);
```

APPENDIX A-continued

PSEUDOCODE IMPLEMENTATION

```
%Analysis
%IRF Deconvolution
For i=1:voxel in kidneyMask
IRF(i,:)=deconvTSVD(data_list(i,:),AIF_TIC);
end
%RTT calculation
%For both kidney
TIC_col=mean(data_list_all(index_col,:),1);
p1=curve_fit_log(time_list,TIC_col);
RTT_all=p1(2);
%for left and right separately
TIC_col_left=mean(data_list_all(index_col_left,:),1);
TIC_col_right=mean(data_list_all(index_col_right,:),1);
RTT_left =curve_fit_log(time_list,TIC_col_left);
RTT_right =curve_fit_log(time_list,TIC_col_right);
%SRF calucation
Calculate_SRF_right( );
Calculate_SRF_left( );
SRF_all=SRF_left+SRF_right;
SRF_left=SRF_left/SRF_all;
SRF_right=SRF_right/SRF_all;
%TTP calculation
%for local parameters
For i=1:voxel in kidneyMask
TTP(i)=findPeak(TIC(I,:))
End
%for global parameters
TTP_left=mean(TTP(index_cortex_left));
TTP_right=mean(TTP(index_cortex_right));
TTP_all=0.5*(TTP_left+TTP_right);
%RBF calculation
For i=1:voxel in kidneyMask
RBF(i)=max(IRF(I,:))
End
%More parameters calculation
GFRCalculation( );
RVDCalculation( );...
%save parameters
SaveParameters( );
```

What is claimed is:

1. A computer implemented method for quantitative-organ-assessment comprising:

(a) obtaining a time series of MRI images in a subject comprising:

(i) acquiring pre-contrast MRI images of the organ;

(ii) introducing an MRI contrast-enhancing agent into the subject; and (iii) obtaining a time-series of MRI images;

(b) storing the MRI images obtained in the absence and presence of an MRI contrast-enhancing substance as a dataset, wherein the dataset comprises intensities associated with voxels at each time point in the time series of MRI images;

(c) partitioning voxels within the dataset into clusters, each cluster containing voxels with similar time-intensity curves by using a Gaussian-mixture-model on principle component space;

(d) distinguishing the organ clusters from background clusters by using a knowledge-based framework comprising applying fuzzy logic based on organ specific standards;

(e) distinguishing the cluster into different inner compartments of the organ by using a physiological spatial model comprising transformation from time-intensity space into the physiological space, wherein the transformation is performed by using the function:

$$SI(t) = \frac{P2 + (P5 \cdot t)}{\{1 + \exp(-P4 \cdot (t - P3))\}^2},$$

to solve for the parameters P2, P3, P4 and P5; wherein P2 is related to the magnitude of baseline and peak signal, P3 is the approximate time of the maximum rate of increase, P4 denotes the slope of the enhancement and P5 describe the trends of excretion, for inner compartments recognition, and (f) computing functional characteristics and parameters of the organ from aggregate intensity-versus-time characteristics of the voxels within the clusters.

2. The computer implemented method of claim 1, further comprising visually displaying the assessment of the organ.

3. The computer implemented method of claim 1, wherein the dataset is compressed into fewer dimensions utilizing principal component analysis.

4. The computer implemented method of claim 1, wherein the clusters are formed using a finite-Gaussian mixture model.

5. The computer implemented method of claim 1, wherein the organ is any one or more of abdomen, brain, breast, heart, liver, lung, neck, pelvis, the musculoskeletal system, ovaries, spine, kidney or prostate.

6. A method for determining the prognosis of kidney disease in a subject in need thereof comprising:

(a) obtaining a quantitative-renal-assessment of the subject by the method of claim 1;
(b) comparing the quantitative renal assessment from the subject with a quantitative renal assessment from a control subject, wherein a difference in at least one or more morphological or functional parameter between the subject and the control subject is indicative of poor prognosis in the subject.

7. A method for determining a treatment course in a subject with a renal disorder comprising:

(i) obtaining a quantitative-renal-assessment of the subject by the method of claim 1; and
(ii) determining a treatment course based on the quantitative-renal-assessment.

8. A computer system comprising one or more processors wherein the computer system is operable to access MRI data and executes a software application implementing the method of claim 1.

9. An article comprising one or more non-transitory machine-readable media storing instructions operable to cause one or more machines to perform operations, wherein the operations comprise implementing the method of claim 1.

10. A non-transitory computer readable recording medium including programmed instructions, wherein the instructions, when executed by a computer that includes a display unit for sequentially displaying time-series images, causes the computer to execute the method of claim 1.

11. Non-transitory computer readable media comprising instructions executable by one or more processors that when executed by one or more processors cause the one or more processors to perform the method of claim 1.

* * * * *